(12) United States Patent
Mehta

(10) Patent No.: US 9,795,489 B2
(45) Date of Patent: Oct. 24, 2017

(54) SYSTEM FOR A KNEE PROSTHETIC

(71) Applicant: Krishnachandra Chandrashanker Mehta, Ahmedabad (IN)

(72) Inventor: Krishnachandra Chandrashanker Mehta, Ahmedabad (IN)

(73) Assignee: L&K BIOMED CO., LTD, Seoul (KR)

( * ) Notice: Subject to any disclaimer, the term of this patent is extended or adjusted under 35 U.S.C. 154(b) by 0 days.

(21) Appl. No.: 14/216,128

(22) Filed: Mar. 17, 2014

(65) Prior Publication Data

US 2014/0200674 A1    Jul. 17, 2014

Related U.S. Application Data

(63) Continuation of application No. PCT/IN2013/000490, filed on Aug. 12, 2013.

(Continued)

(30) Foreign Application Priority Data

Nov. 21, 2012   (IN) .......................... 3332/MUM/2012

(51) Int. Cl.
*A61F 2/38*    (2006.01)
*A61F 2/30*    (2006.01)

(52) U.S. Cl.
CPC .... *A61F 2/389* (2013.01); *A61F 2002/30065* (2013.01); *A61F 2002/30324* (2013.01);

(Continued)

(58) Field of Classification Search
CPC ................................... A61F 2/38; A61F 2/389
See application file for complete search history.

(56) References Cited

U.S. PATENT DOCUMENTS 3,798,679 A  *  3/1974  Ewald .................... 623/20.31
4,231,120 A  *  11/1980  Day ........................ 623/23.24

(Continued)

FOREIGN PATENT DOCUMENTS

| CN | 101039637 | 2/2011 |
|---|---|---|
| WO | 2009/105496 A1 | 8/2009 |
| WO | WO2009105496 | 8/2009 |

OTHER PUBLICATIONS

Richards Maximum Contact R.M.C. Total Kee, Total Joints Orthopedic, 1982, 1 page.

(Continued)

*Primary Examiner* — Marcia Watkins
(74) *Attorney, Agent, or Firm* — Loza & Loza, LLP; Jessica W. Smith

(57) ABSTRACT

A knee replacement system for enabling natural knee movement in a leg comprising a prosthetic is provided. The prosthetic includes a tibial portion at least partially implantable on a resected surface of a tibia; a plate portion attached to the tibial portion and at least partially implantable in a meniscal space; wherein the plate portion comprises a top surface having a medial recess and a lateral recess and a bottom surface attached to a top surface of the tibial portion wherein the tibial portion and the plate portion are one piece, wherein a medial side surface, a lateral side surface, a posterior side surface and an anterior side surface are attached to at least a portion of the top surface and at least a portion of the bottom surface and defining a medial side edge, a lateral side edge, a posterior side edge and an anterior side edge respectively, where in at least a portion of one of the medial side edge, lateral side edge, posterior side edge, and anterior side edge is oblique.

20 Claims, 28 Drawing Sheets

Related U.S. Application Data

(60) Provisional application No. 61/792,658, filed on Mar. 15, 2013.

(52) U.S. Cl.
 CPC ........... *A61F 2002/30326* (2013.01); *A61F 2002/30878* (2013.01); *A61F 2002/30884* (2013.01)

(56) References Cited

U.S. PATENT DOCUMENTS

| | | | |
|---|---|---|---|
| 4,769,039 A * | 9/1988 | Horber | 623/20.32 |
| 5,658,342 A | 8/1997 | Draganich et al. | |
| 5,683,467 A | 11/1997 | Pappas | |
| 5,879,394 A | 3/1999 | Ashby et al. | |
| 6,013,103 A | 1/2000 | Kaufman et al. | |
| 6,120,543 A * | 9/2000 | Kubein-Meesenburg et al. | 623/23.42 |
| 6,235,060 B1 * | 5/2001 | Kubein-Meesenburg et al. | 623/20.31 |
| 6,264,697 B1 | 7/2001 | Walker | |
| 6,379,388 B1 | 4/2002 | Ensign et al. | |
| 6,558,421 B1 | 5/2003 | Fell et al. | |
| 6,866,684 B2 * | 3/2005 | Fell | A61F 2/38 623/20.3 |
| 7,175,665 B2 | 2/2007 | German et al. | |
| 7,261,740 B2 | 8/2007 | Tuttle et al. | |
| 7,326,252 B2 | 2/2008 | Otto et al. | |
| 7,625,407 B2 | 12/2009 | Akizuki et al. | |
| 7,713,305 B2 | 5/2010 | Ek | |
| 7,771,483 B2 | 8/2010 | Justin et al. | |
| 7,998,205 B2 | 8/2011 | Hagen et al. | |
| 8,114,165 B2 | 2/2012 | Rhodes et al. | |
| 2003/0060885 A1 * | 3/2003 | Fell et al. | 623/14.12 |
| 2007/0067032 A1 | 3/2007 | Felt et al. | |
| 2007/0185581 A1 * | 8/2007 | Akizuki | A61F 2/389 623/20.32 |
| 2008/0243258 A1 | 10/2008 | Sancheti | |
| 2009/0088861 A1 | 4/2009 | Tuke et al. | |
| 2009/0226068 A1 | 9/2009 | Fitz et al. | |
| 2010/0016976 A1 | 1/2010 | Siebel | |
| 2010/0016980 A1 | 1/2010 | Donno et al. | |
| 2010/0036499 A1 | 2/2010 | Pinskerova | |
| 2011/0022179 A1 | 1/2011 | Andriacchi et al. | |
| 2011/0082559 A1 | 4/2011 | Hartdegen et al. | |
| 2011/0130843 A1 | 6/2011 | Otto et al. | |
| 2011/0264097 A1 | 10/2011 | Hodorek et al. | |
| 2011/0313534 A1 | 12/2011 | Ries et al. | |
| 2012/0022660 A1 | 1/2012 | Wentorf | |

OTHER PUBLICATIONS

Muller, S.D. et al.; "Should we reconsider all-polyethylene tibial implants in total knee replacement?"; the Journal of Bone and Joint Surgery, vol. 88-B, No. 12, Dec. 2006, pp. 1596-1602.

Gioe, Terence J. et al.; "The All-Polyethylene Tibial Component in Primary Total Knee Arthroplasty"; the Journal of Bone and Joint Surgery, 2010; 92:478-87; doi:10.2106/JBJS.I.00842, pp. 478-487.

Chinese Patent Appl. No. 201380060118. Applicant: K.C. Mehta. Office Action dated Apr. 19, 2016.

European Patent Appln. No. 13856134. Applicant: K.C. Mehta. Search Report dated May 23, 2016.

Singapore Patent Appln. No. 11201502920W. Applicant: K.C. Mehta. Written Opinion dated Feb. 26, 2016.

* cited by examiner

SYSTEM FOR A KNEE PROSTHETIC

CROSS-REFERENCE TO OTHER APPLICATIONS

This application claims the benefit of U.S. provisional application Ser. No. 61/792,658, filed on Mar. 15, 2013, and entitled, "Knee Replacement Prosthetic." This application is a continuation application of International Application No. PCT/IN2013/000490, filed on Aug. 12, 2013, and entitled, "Knee Replacement Prosthetic." This application also claims the benefit of Indian Application No. 3332/MUM/2012, filed on Nov. 21, 2012.

FIELD OF INVENTION

The present invention is directed to a system and method for enabling natural knee movement after knee arthroplasty, specifically an implantable knee prosthetic that enables natural knee movement, and methods of using the same.

BACKGROUND

Total or partial knee replacement surgery is called knee arthroplasty. Total or partial knee replacement may be done to relieve knee pain, for example, knee pain caused by arthritis. Although there are many types of arthritis, most knee pain is caused by three types: osteoarthritis, rheumatoid arthritis, and post-traumatic arthritis, and the like. Prosthetic knee implants are utilized to repair and/or replace damaged bone and tissue in the human body. For example, a knee prosthetic may include a tibial component that is attached to a resected or natural proximal tibia, a femoral component attached to a resected or natural or natural distal femur, and a meniscal component coupled with the tibial component and the femoral component. Usually, the meniscal component is used to provide an appropriate level of friction and contact area at the interface between the femoral component attached to the tibial component via a locking mechanism, or the like. The locking mechanism may present problems such as, but not limited to, backside wear and/or micromovements between two surfaces. However, these prosthetics may not allow for natural knee movement when implanted and thus, there is a need for the same. For example, these prosthetics may not provide the appropriate level of flexion and/or freedom of rotation and/or may be mobile-bearing prosthetics.

SUMMARY OF INVENTION

A knee replacement system for enabling natural knee movement in a leg is provided. The system includes a prosthetic having a tibial portion at least partially implantable on a resected surface of a tibia; a plate portion attached to the tibial portion and at least partially implantable in a meniscal space. Preferably, the plate portion compromises a top surface having a medial recess and a lateral recess articulating with medial and lateral condyle of femur or femoral component respectively; and a bottom surface attached to a top surface attached to a top surface of the tibial portion. Preferably, the tibial portion and the plate portion are one piece. In other embodiments, the tibial portion and the plate portion are not one piece.

Preferably, the prosthetic consists essentially of polyethylene. The plate portion may further include a medial side surface attached to at least a portion of the top surface and at least a portion of the bottom surface and defining a medial side edge; a lateral side surface attached to at least a portion of the bottom surface and defining a lateral side edge; a posterior side surface attached to at least a portion of the top surface and at least a portion of the bottom surface and defining a posterior side edge; and an anterior side surface attached to at least a portion of the top surface and defining an anterior side edge. Preferably, at least a portion of one of the medial side edge, lateral side edge, posterior side edge, or anterior side edge is oblique. Preferably, the plate portion is not comprised essentially of a metal.

Preferably, at least a portion of the medial side edge and at least a portion of the lateral side edge are oblique. Preferably, at least a portion of the posterior side edge is oblique. Preferably, at least a portion of the anterior side is oblique. Preferably, each of the medial side edge and the lateral side edge is oblique from about 15 to about 60 degrees. Preferably, the posterior side edge is oblique from about 15 to about 60 degrees. Preferably, the anterior side is oblique from about 15 to about 60 degrees. The system may further comprise a femoral component, wherein the femoral component comprises a medial condyle and a lateral condyle, wherein the femoral component is at least partially implantable on a resected portion of the femur. The system may further include a patellar component, coupled to the femoral component and implantable on an anterior distal portion of the femur that is adapted to provide a contacting surface for a patella of the leg.

In a preferred embodiment, the prosthetic comprises: a tibial portion at least partially implantable on a resected surface of a tibia; a plate portion attached to the tibial portion, and at least partially implantable in a meniscal space. Preferably, the plate portion comprises a top surface having a medial recess and a lateral recess for receiving a medial condyle and a lateral condyle of a femur or a femur component. Preferably, the prosthetic is implantable as one piece. Preferably, the prosthetic includes an anterior side surface center axis; a first protrusion on a first side of anterior side surface; and a second protrusion on a second side of anterior side surface. Preferably, each of the anterior side surface center axis, the first protrusion, and the second protrusion comprise a height, wherein the height of the anterior side surface center axis is from about 14 mm to about 21 mm the height of the first and second protrusion is from about 11 mm to about 18 mm.

In a preferred embodiment, a method of implanting a prosthetic of the present invention is provided. The method includes resecting a tibia of a knee.

In a preferred embodiment, a knee replacement system for enabling natural knee movement comprising a prosthetic is provided. The prosthetic includes a plate portion at least partially implantable in a meniscal space. Preferably, the plate portion includes a medial side surface attached to at least a portion of the bottom surface and defining a medial side edge; a lateral side surface attached to at least a portion of the top surface and at least a portion of the bottom surface and defining a lateral side edge; a posterior side surface attached to at least a portion of the top surface of the bottom surface and defining a posterior side edge; an anterior side surface attached to at least a portion of the top surface and at least a portion of the bottom surface and defining an anterior side edge. Preferably, at least a portion of one of the medial side edge, lateral side edge, posterior side edge, or anterior side edge is oblique.

BRIEF SUMMARY OF DRAWINGS

The invention may be more readily understood by referring to the accompanying drawing in which.

DETAILED DESCRIPTION OF THE INVENTION

Figure 1:
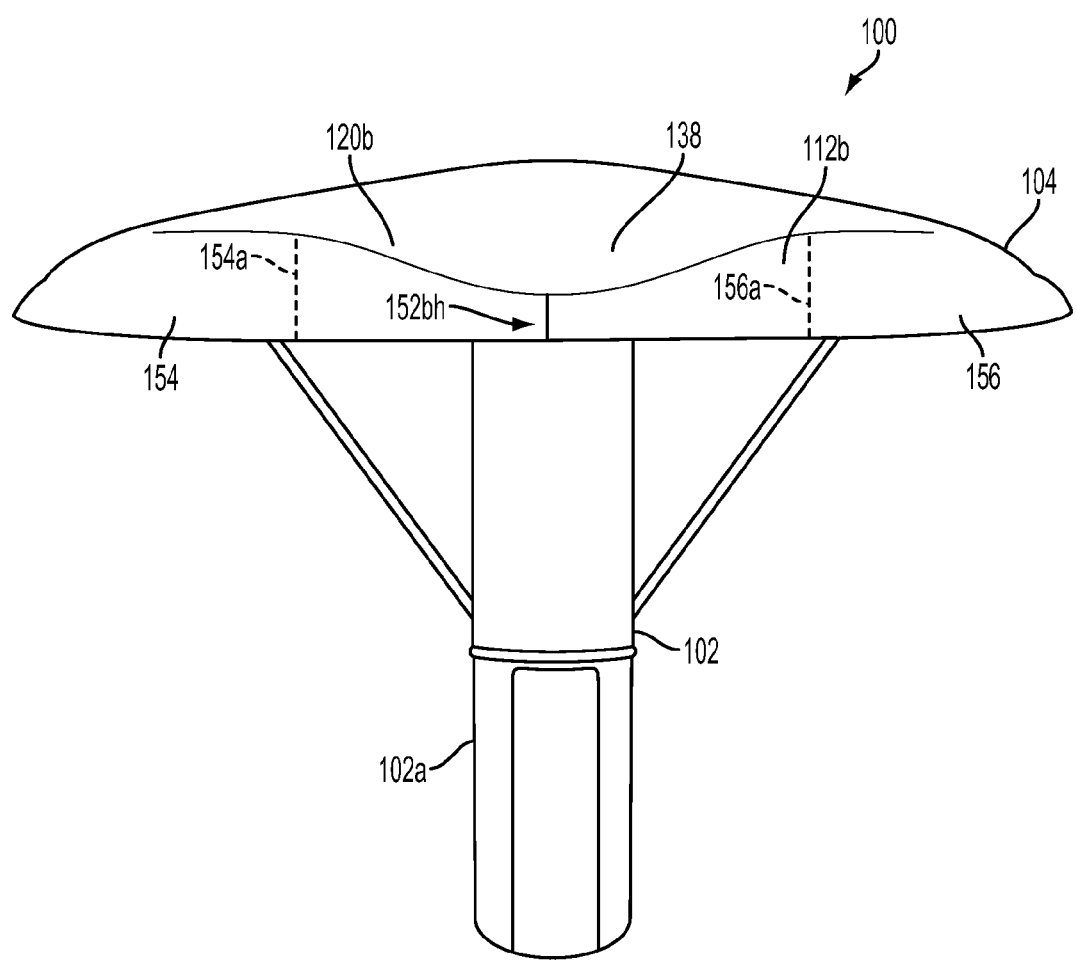
FIG. 1 is an anterior view of a prosthetic of the present invention.

It will be appreciated that terms such as "front", "back", "top", "bottom", "left", "right", "horizontally", "up", "down", "upwardly", "downwardly", "side", "medial" and/or "lateral" used herein are merely for ease of description and refer to the orientation of the components as shown in the figures. It is to be understood that any orientation of the prosthetic, and the components thereof described herein, is within the scope of the present invention.

"Anterior" refers to direction generally toward the front of the patient. As used herein, "posterior" refers to an opposite or substantially opposite direction of anterior, i.e., generally towards the back of the patient.

"Attached" and/or "attached to" and/or any grammatical version thereof, may refer to "formed from" and/or "joined" and/or "connected" together. As used herein, for example, if two components are attached, they may be formed from one piece, or they may not be formed from one piece, i.e., they may be joined together via any means known in the art. If they are formed from piece, for example, they do not need to be joined together.

"One piece" refers to a component that does not include portions components that are engaged/locked together, i.e., a component that is implantable as one piece.

"Edge", or any grammatical version thereof, may refer to a line or area in which two surfaces meet, and these two surfaces may be perpendicular to each other, or at any other degree in relation to each other.

"Oblique edge" or any grammatical version thereof, may mean "sloping face" and/or "beveled edge" and/or "chamfer" (i.e. plane) where two surfaces meet and the two surfaces are neither parallel nor perpendicular to each other. As used herein, "oblique edge," or any grammatical version thereof, may refer to a line or area (i.e., plane, wherein two surfaces meet and the two surfaces are neither parallel nor perpendicular to each other. For example, an oblique edge may be neither parallel nor perpendicular to a given line, surface, or edge, and is slanting or sloping. For example, if the oblique edge has a surface area, it may be in a different plane than the planes of the sides/surfaces forming it. As used herein, "oblique edge" may refer to an edge that is a line; curved line or area. Additionally, the oblique edges of the invention may be identified by degrees. It is to be understood that the numerical value of the degrees, i.e. (45 degrees) is preferably determined by the plane of the top surface relative to the plane of the oblique edge or sloping surface. For example, if an oblique edge is 50 degrees, then the plane of the oblique edge (extrapolated if need be). As further described below, these oblique edges are preferably located on the plate portion of the knee implant. Since the plate portion is preferably oval-shaped or substantially oval-shaped, each of the edges preferably are curved or substantially curved. As such, there may be no definite "boundary" between one edge/oblique edge and another edge/oblique edge (as there is with objects that are, for example, square in shape). As such, reference to, for example, an edge such as "medial side edge" may be approximate and refer to the edge that is substantially on the medial side of the implant.

"Prosthetic" may be interchangeable with "implant," or "medical device." "Affix" may refer to any means known to attach to a bone surface, i.e., for example, but not limited to, attached to a resected surface. For example, the prosthetic may be attached to a resected surface via cement or the like.

"Polyether," or "polyethylene," refers to any type of plastic now known or later contemplated and used in prosthetics.

"Protrusion", "first protrusion," and/or "second protrusion" may refer to the side surfaces on either side of the anterior side surface of the prosthetic as described herein.

"Height" and/or "height at center axis" refers to the height at the center of the component/surface, or substantially at the center of the component surface. For example, reference to "height at center of protrusion" may refer to the height at the middle of, or substantially at the middle of, the portion of the anterior surface that protrudes.

Figure 7:
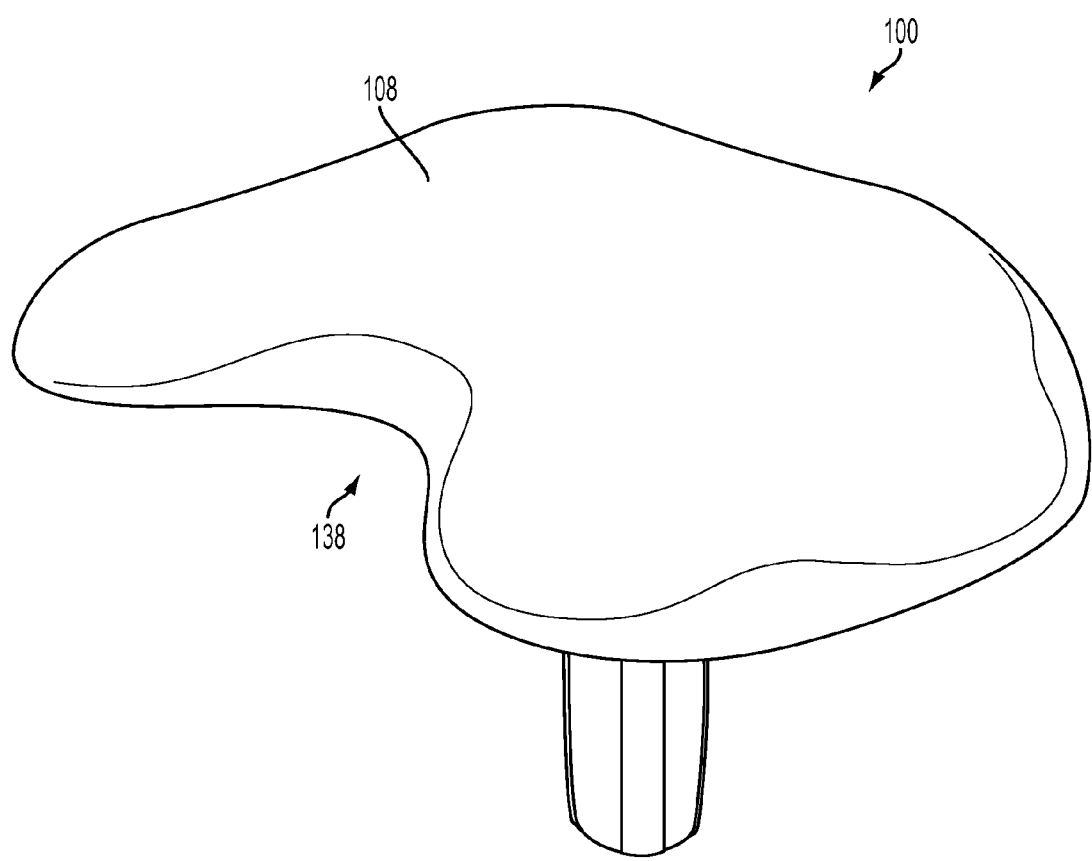
FIG. 7 is a perspective view of FIG. 1.
Figure 28:
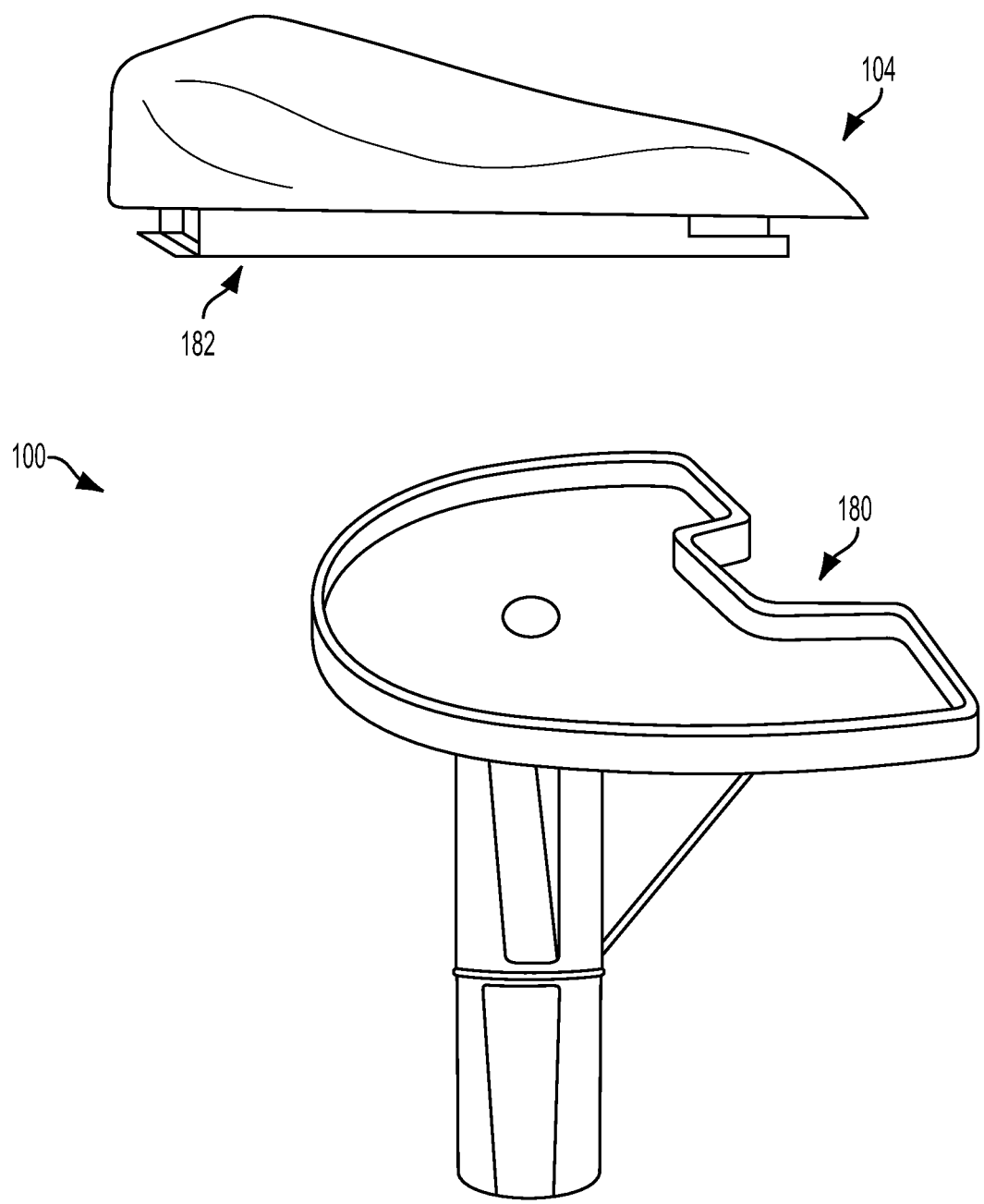
FIG. 28 is an exploded view of one embodiment of the present invention.

Referring to FIGS. 1-28, a preferred embodiment of a prosthetic is shown and described. Generally, prosthetic 100 includes a tibial portion 102 and a plate portion 104. Preferably, tibial portion 102 and plate 104 portion are one piece. As such, there is no need to use a locking mechanism or the like to attach tibial portion 102 to plate 104 portion, since they are preferably formed from one piece. When implanted, tibial portion 102 may be affixed at least partially to a resected or natural tibia, and plate portion 104, may be disposed at least partially in a joint space of a knee, i.e., between the tibial and femoral bones, or a meniscal space. Preferably, plate portion 104 comprises top surface 108, and top surface 108 includes an articulating surface as shown in FIG. 9. Preferably, and as shown in FIG. 2, plate portion 104 portion is adapted to receive/engage/attach to, etc. a femoral component 130 via, for example, its articulating surface. Preferably, prosthetic 100 is comprised of polyethylene, i.e., tibial portion 102 and plate portion 104 are both comprised of polyethylene and/or any other plastic, and preferably, prosthetic 100 is not comprised of metal and/or is not substantial comprised of metal. In other embodiments, tibial portion 102 and plate portion 104 are not formed as one piece, i.e., they are formed as separate pieces and are attached/joined together; and/or may be attached/engaged/coupled to each other in any way. In other embodiments, prosthetic 100 does not include tibial portion 102, i.e., tibial portion 102 is omitted. In this manner, plate portion 104 may be used, for example, in connection with any other knee prosthetic component and/or any other tibial portion component now known or later contemplated, and/or may be used in connection with a metal plate. As such, in some embodiments, a metal-backed tibial portion may be attached to the plate portion 104 having a top articulating surface 108 (as shown in FIGS. 7 and 28).

In a preferred embodiment, one or more of the following may be implanted with prosthetic 100: femoral component 130 (as shown in FIG. 2), patellar component 134 (not shown), or any other component needed for total or partial knee replacement now known or later contemplated. Preferably, prosthetic 100 is implanted with femoral component 130. For example, femoral component 130 may be disposed on plate portion 104, i.e., at a top, articulating surface of plate portion 104. Preferably, patellar component 134 is coupled to femoral component 130 and implantable on an anterior distal portion of the femur that is adapted to provide a contacting surface for a patella of a leg. Preferably, patellar component 134 is implantable to replace the patella of the leg. Preferably, it articulates with patellar component 134.

The components used, for example, in connection with prosthetic 100 may be available from known medical device suppliers, such as, but not limited to, Stryker, Zimmer, Depuy and the like. In other embodiments, patellar component 134 may be omitted, i.e., for example, in the event that they do not need to be replaced and/or one or more components of the knee are not resected. In yet other embodiments, any other components for total or partial knee replacement may be used with prosthetic 100 of present invention.

Figure 2:
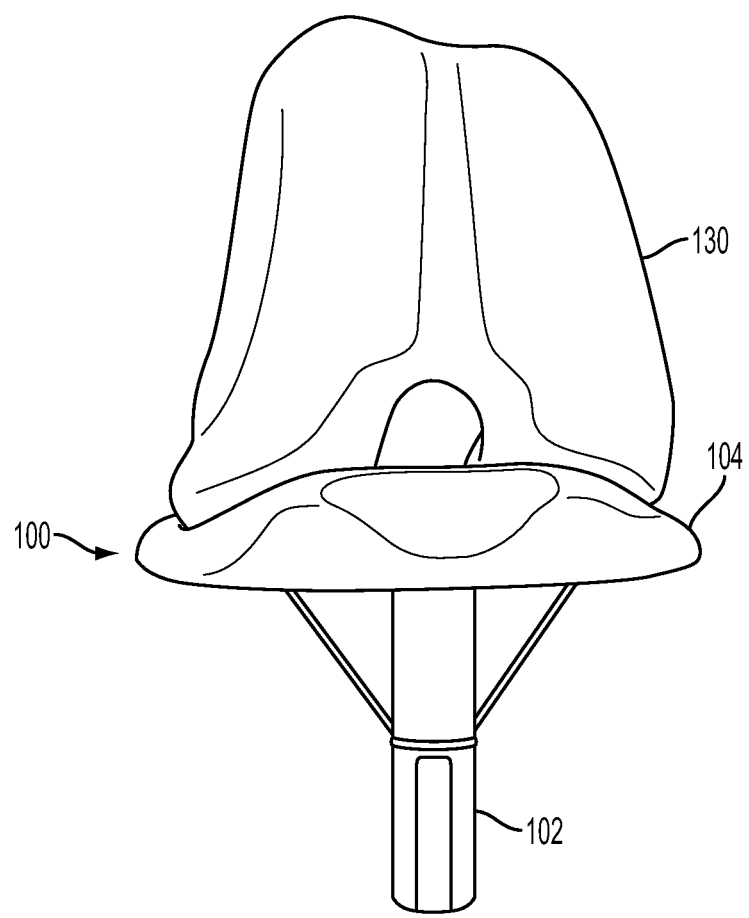
FIG. 2 is an anterior view of the prosthetic of FIG. 1 and having a femoral component.

In a preferred embodiment, and referring to FIG. 1, tibial component 102 includes tibial stem 102*a*. Preferably, at least a portion of tibial stem 102*a* is implantable on a tibia/resected surface of tibia. Preferably, tibia stem 102*a* and tibial component 102 are one piece. In other embodiments, tibial stem 102*a* and tibial component 102 may be separate pieces, and may be attached/engaged/joined together in any way. In yet other embodiments, tibial stem 102*a* is omitted.

Figure 11:
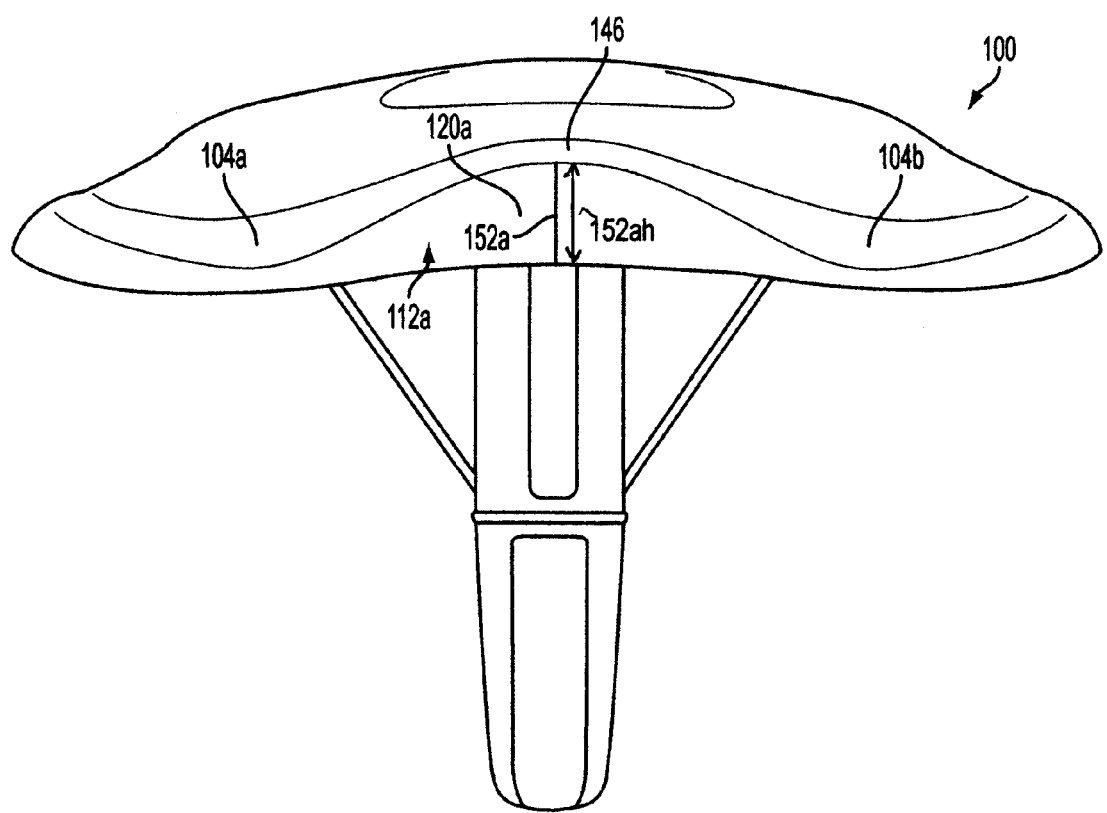
FIG. 11 is a posterior view of the prosthetic of FIG. 1.
Figure 13:
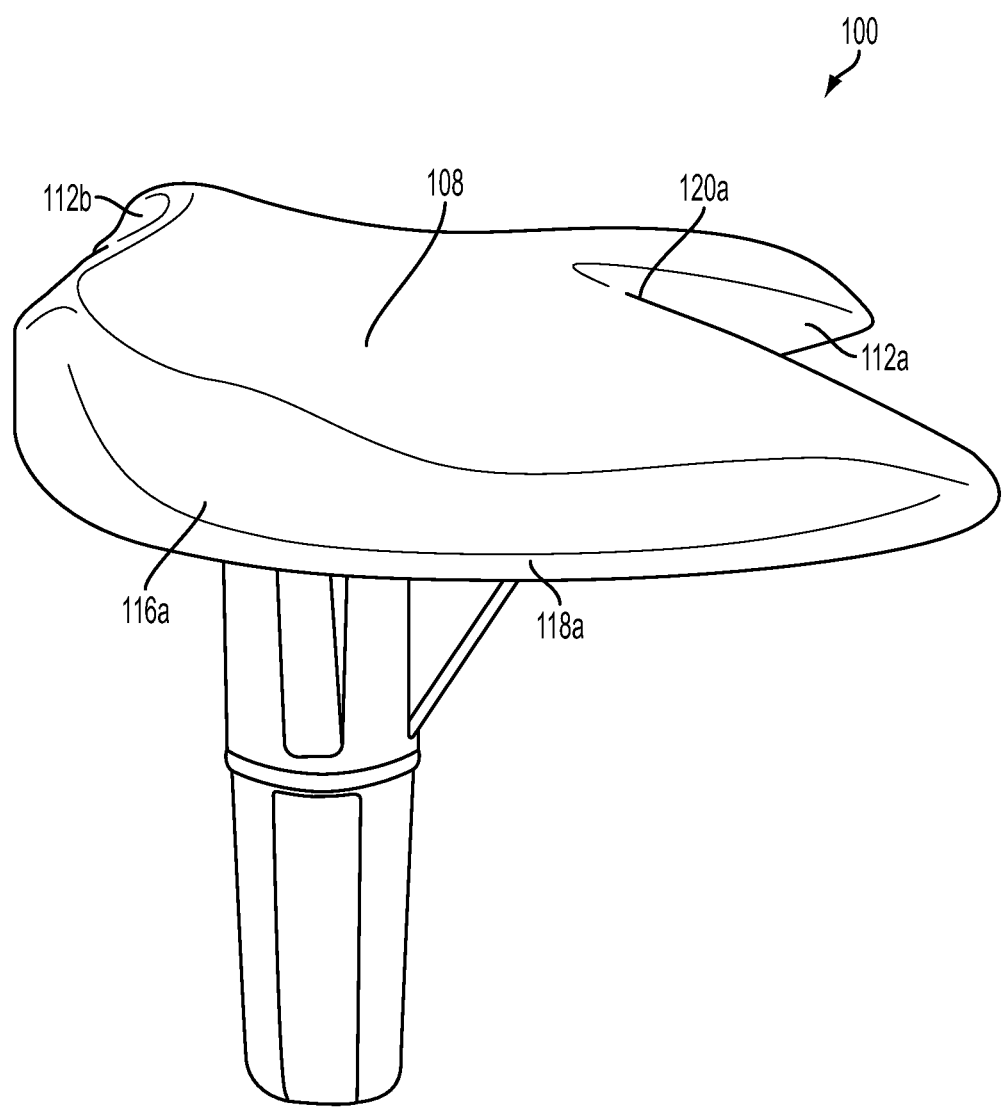
FIG. 13 is a side view of the prosthetic of FIG. 1.
Figure 14:
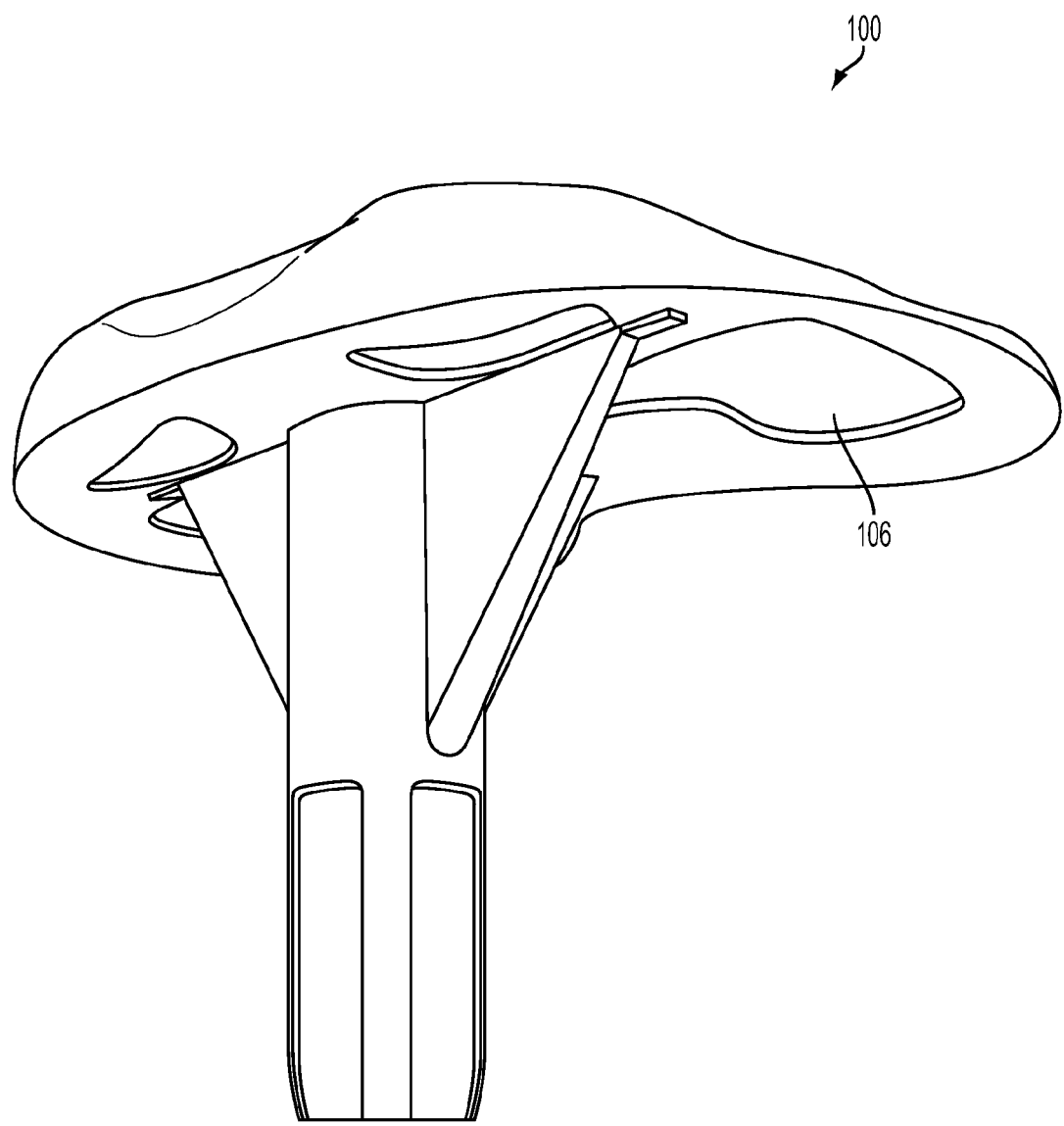
FIG. 14 is a bottom view of prosthetic of FIG. 1.
Figure 15:
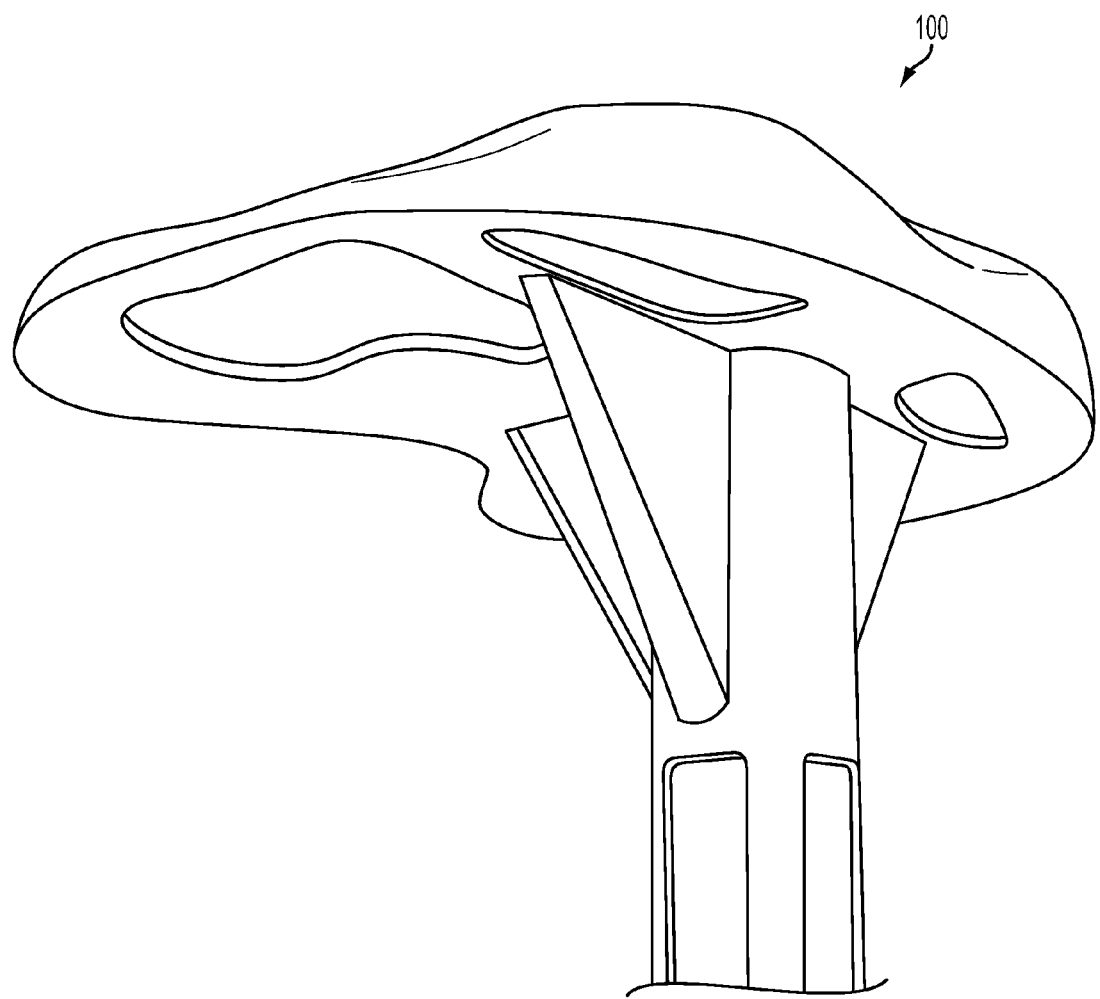
FIG. 15 is a bottom view of the prosthetic of FIG. 1.
Figure 16:
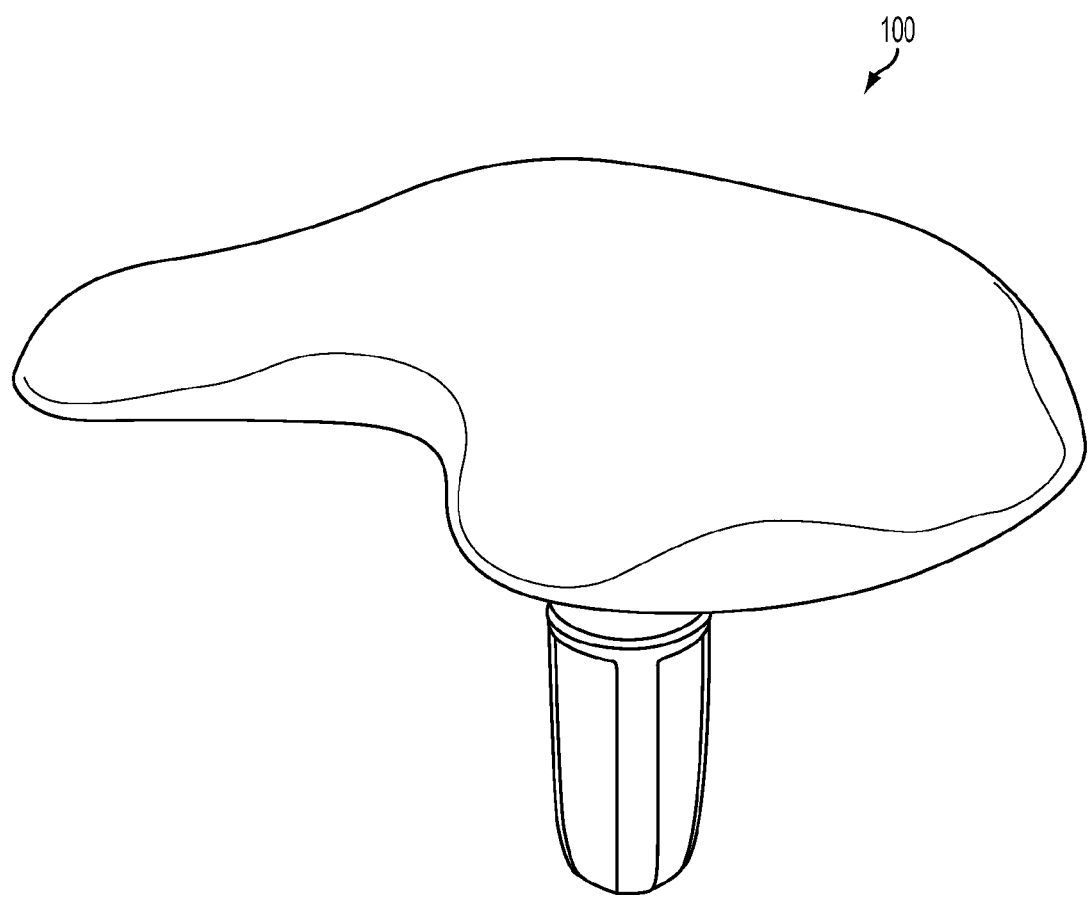
FIG. 16 is a perspective view of the prosthetic of FIG. 1.
Figure 17:
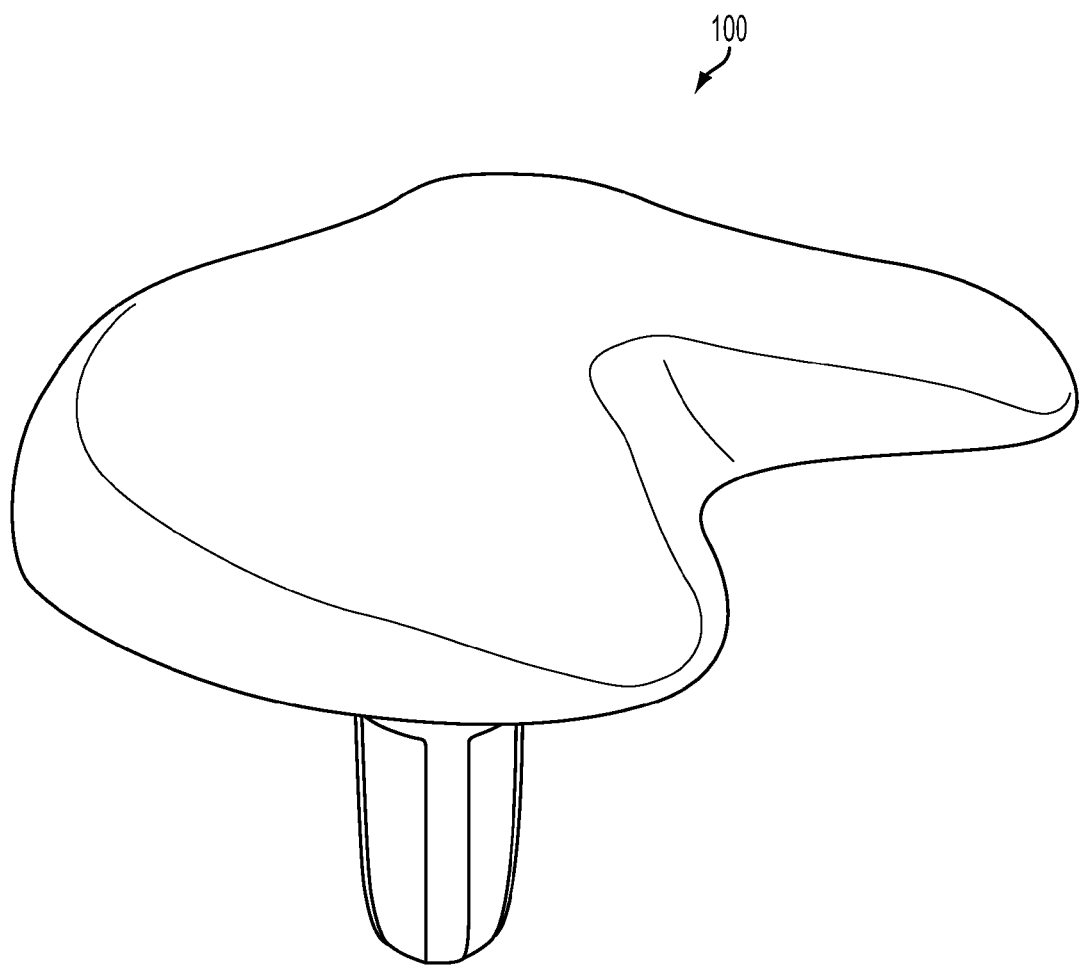
FIG. 17 is a perspective view of the prosthetic of FIG. 1.
Figure 18:
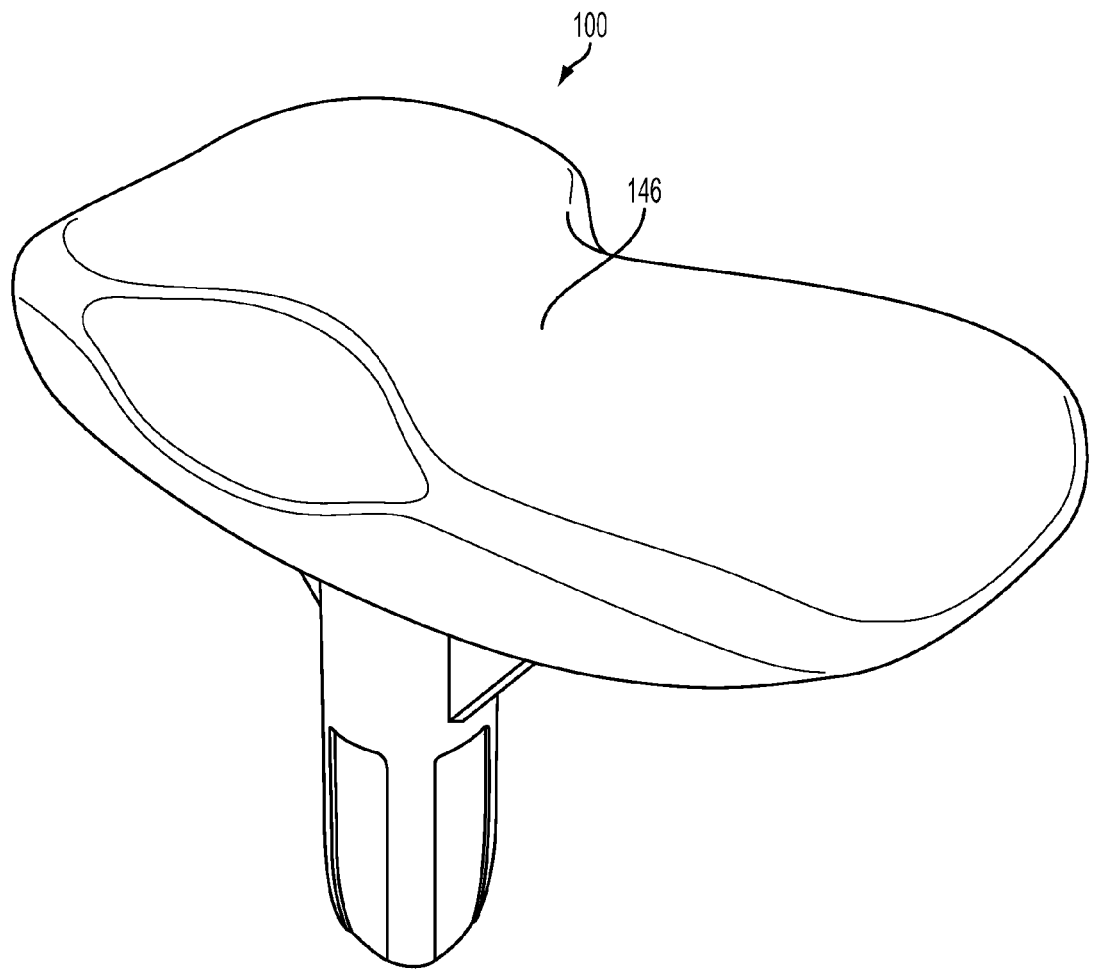
FIG. 18 is a perspective view of the prosthetic of FIG. 1.
Figure 19:
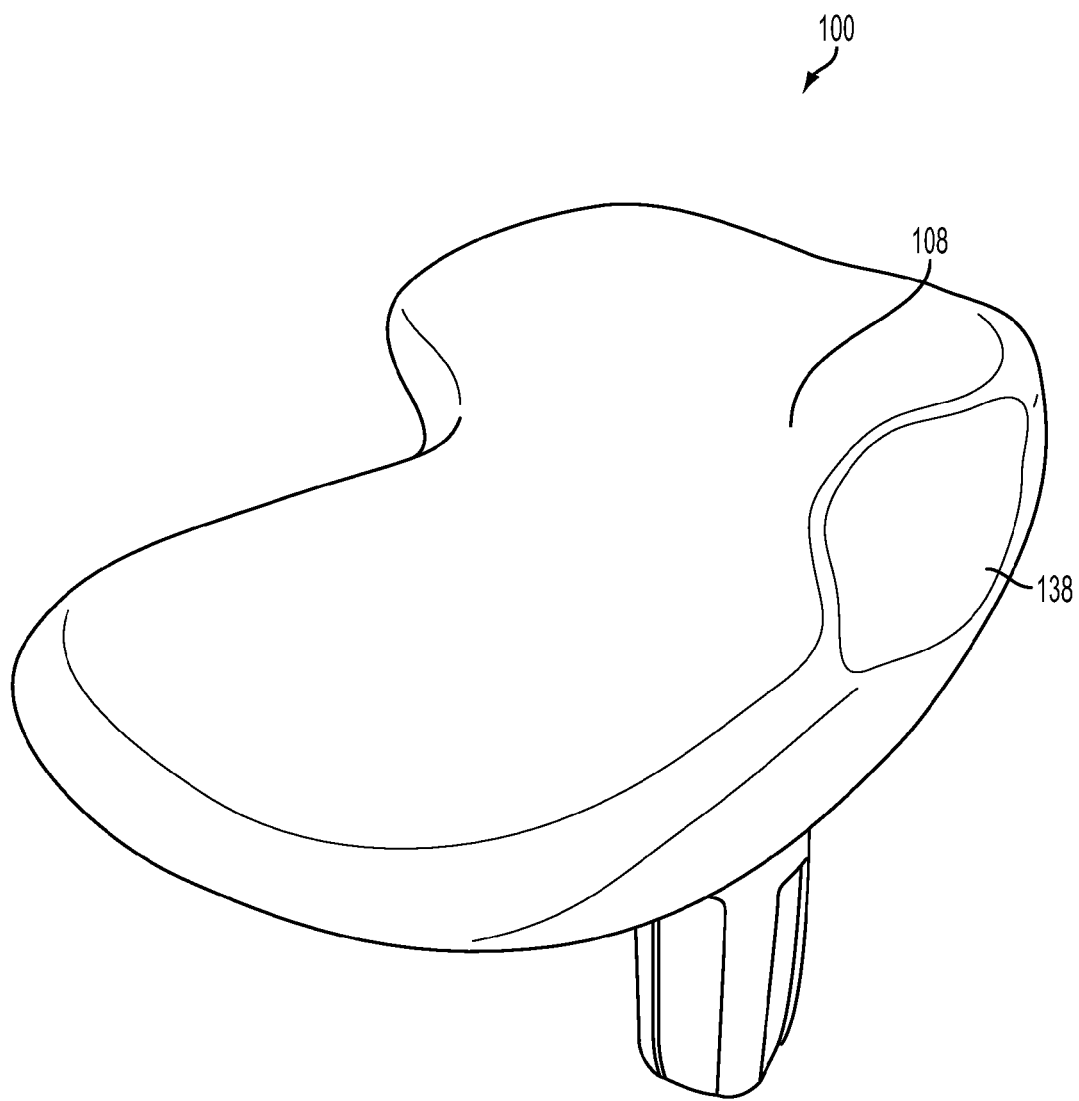
FIG. 19 is a perspective view of the prosthetic of FIG. 1.
Figure 20:
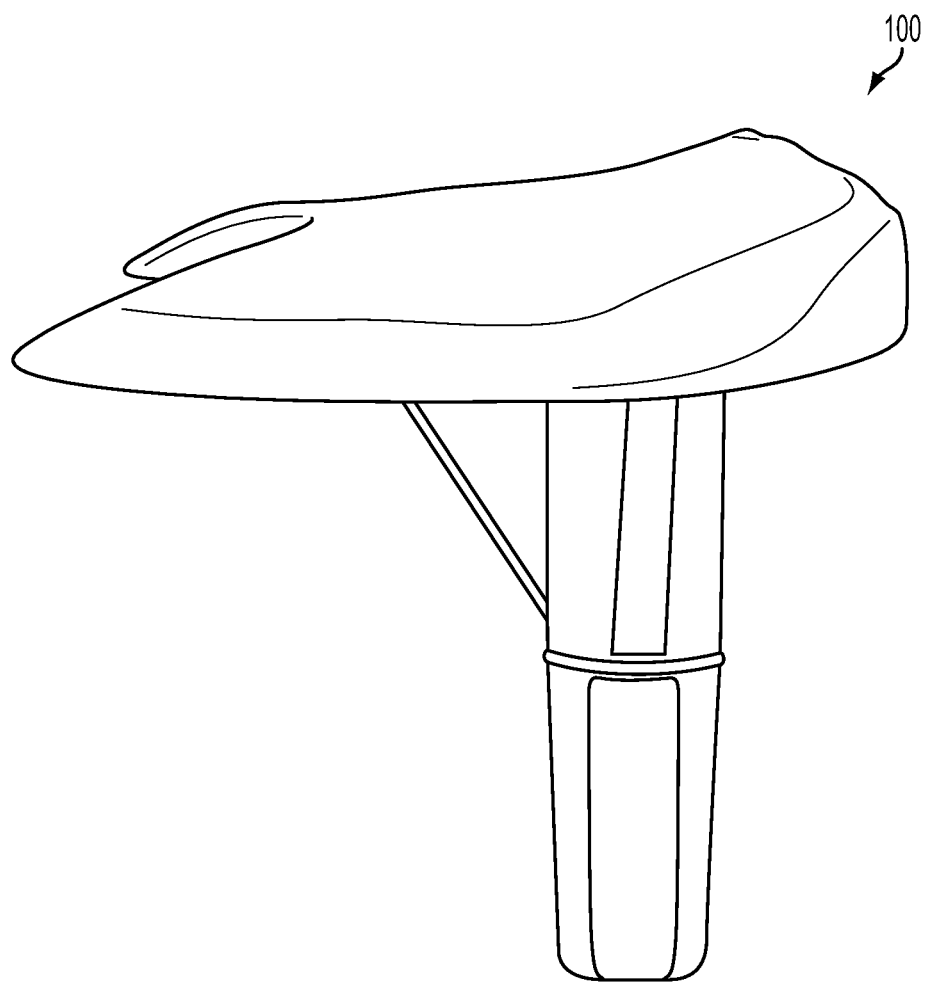
FIG. 20 is a side plan view of the prosthetic of FIG. 1.
Figure 25:
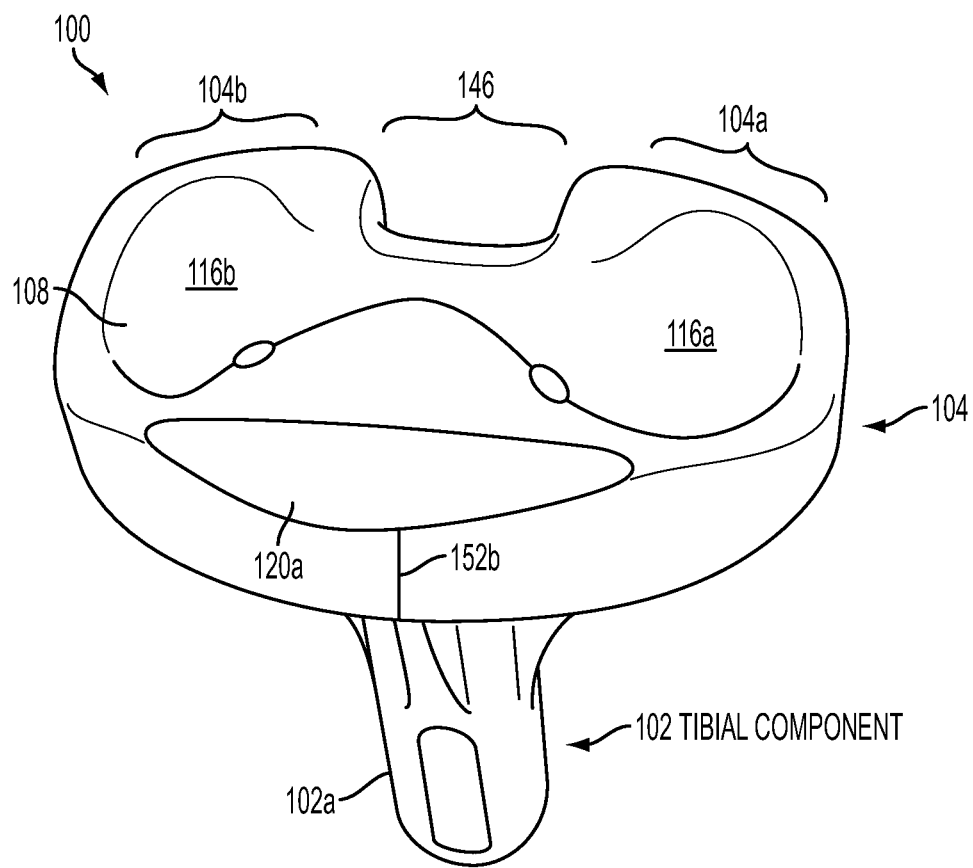
FIG. 25 is a top view of the prosthetic of FIG. 1.

In a preferred embodiment, and referring to FIG. 25, plate portion 104 comprises a medial portion 104*a*, a lateral portion 104*b*, and a middle portion 146. Preferably, middle portion 146 form an arch as shown in FIGS. 11, 13 and 19. Preferably these portions are one piece. Preferably, when prosthetic 100 is implanted into a knee, medial portion 104*a* is situated on the medial side of the knee (i.e., towards the middle side of the body), and lateral portion 104*b* is situated on the lateral side of the knee (i.e., towards the outside of the body), and lateral portion 104*b* is situated on the lateral side of the knee (i.e., towards the outside of the body). As such, it is to be understood that these designations ("medial" and/or "lateral") depend on whether prosthetic 100 is configured for use on the right or left knee, and both are contemplated in the invention described herein. Preferably, presence of arch and/or height scheme as described herein may allow one to sit cross-legged. In other embodiments, medial portion 104*a*, lateral portion 104*b*, and/or middle portion 146 may be formed separately and may be attached/engaged/joined together by any means known in the art. In yet other embodiments, arch is omitted.

Figure 3:
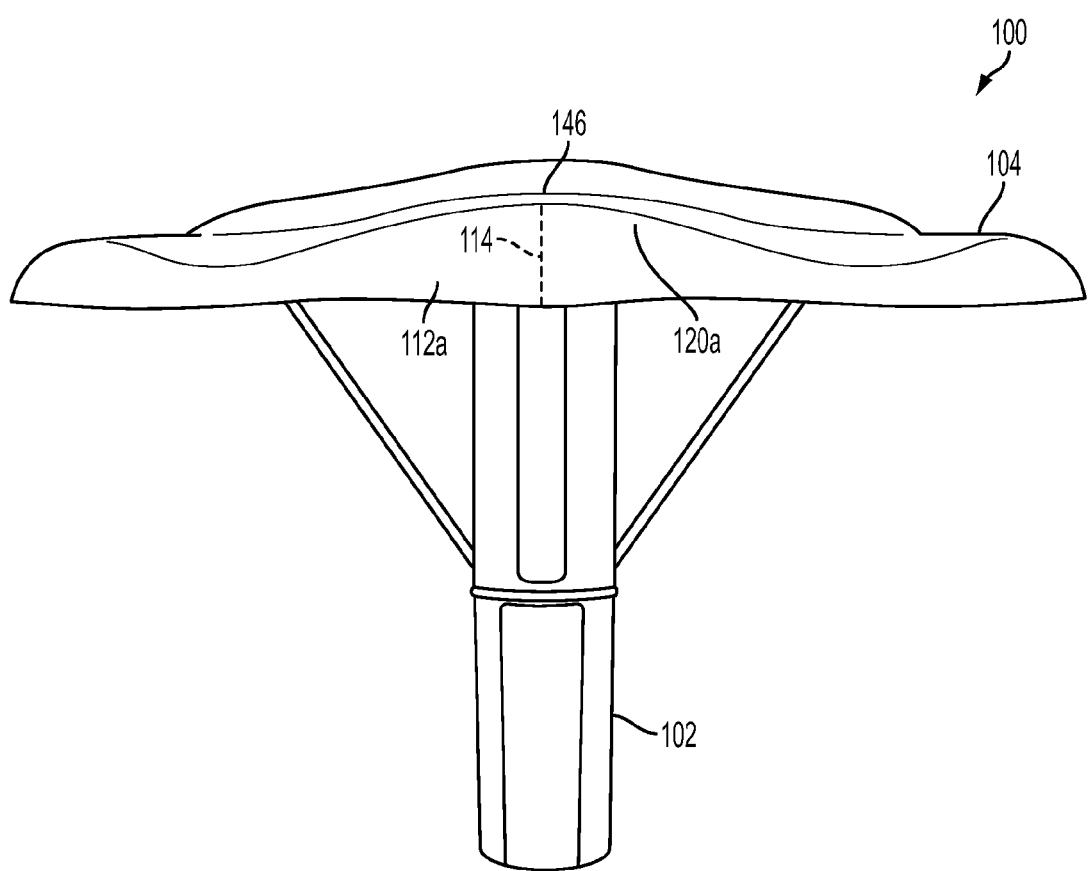
FIG. 3 is a posterior view of the prosthetic of FIG. 1.

In a preferred embodiment, and as shown in FIGS. 3 & 25, center 114 of plate portion 104, i.e., center 114 of middle portion 146, has a height measured from bottom of plate 104 that is the same, or more than, the height at center of each of medial side edge and/or lateral side edge. Preferably, the foregoing heights may be from about 5 mm to about 15 mm, and more preferably, from about 6 mm to about 13 mm. In other embodiments, the height at center 114 is not the same (or is lower) as the height at the center of medial side edge and/or the height at center of lateral side edge.

Figure 23:
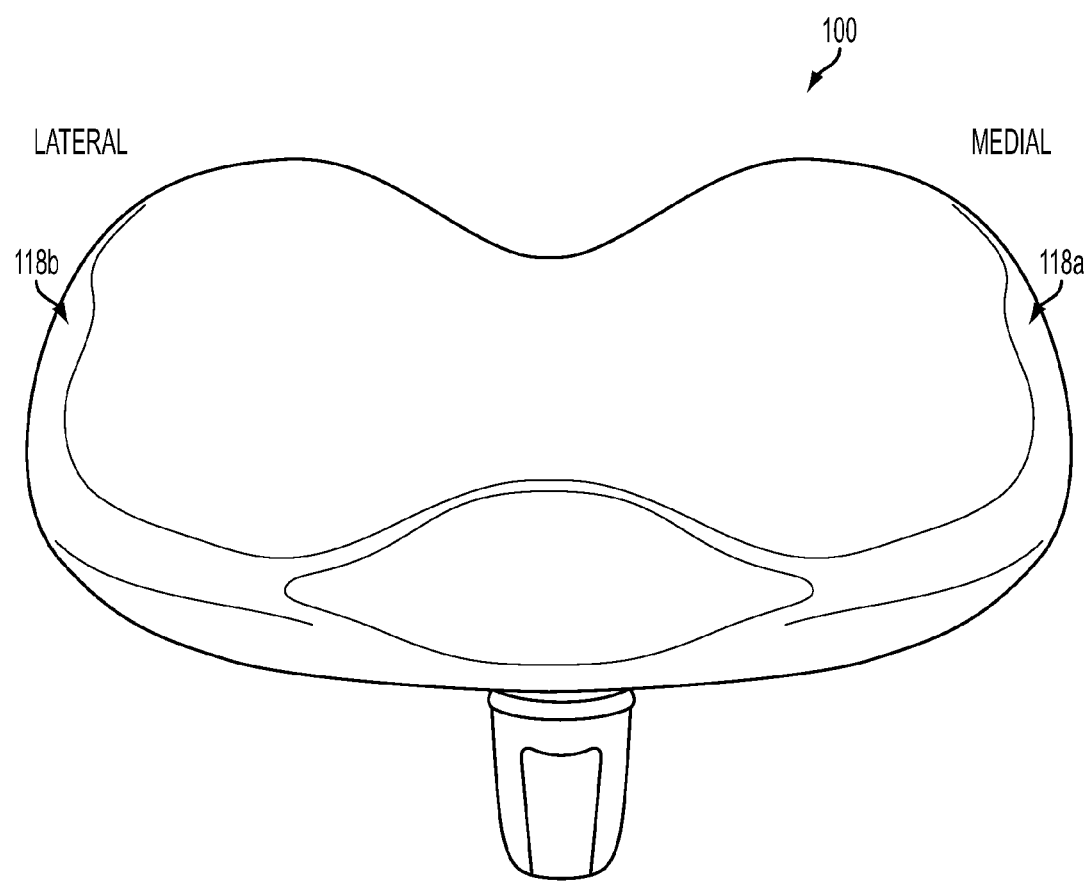
FIG. 23 is a top plan view of the prosthetic of FIG. 1.
Figure 24:
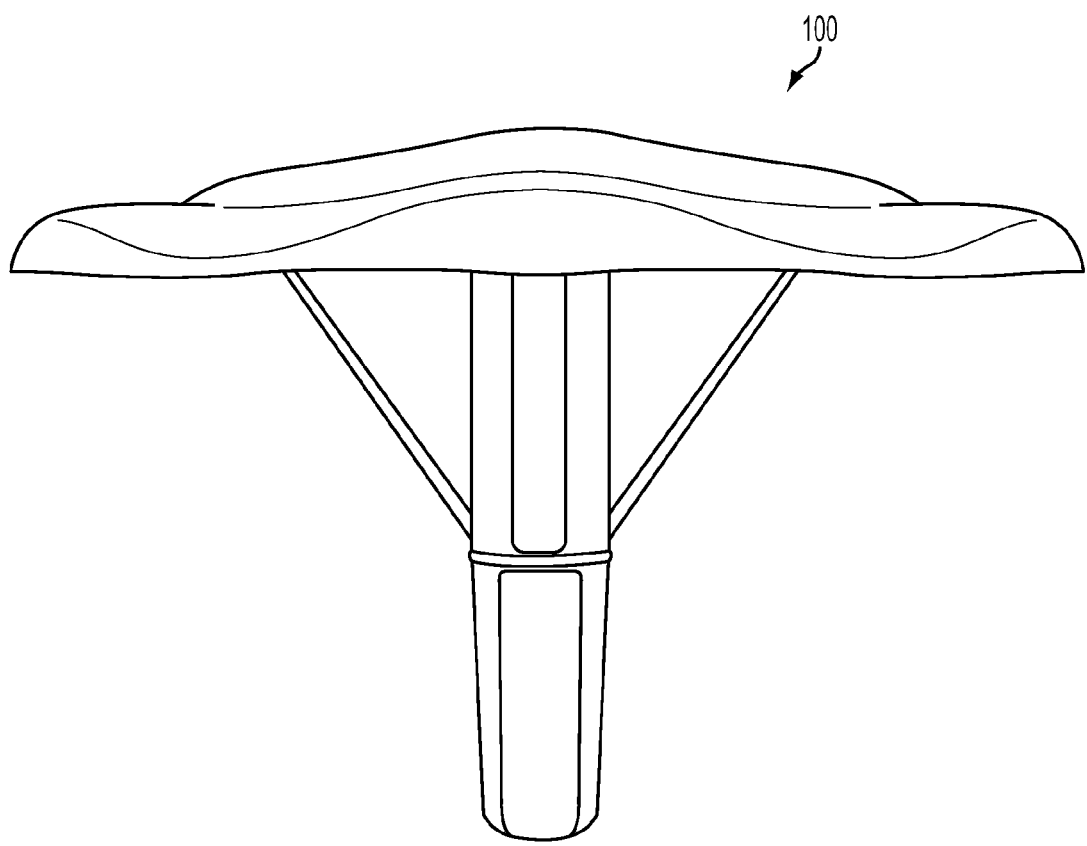
FIG. 24 is a posterior view of the prosthetic of FIG. 1.

In a preferred embodiment, and referring to FIGS. 1, 3, 4, 8, 9, 11, 13, 14, 25, plate portion 104 comprises a top surfaces 108, a bottom surface 106, a medial side surface 110*a*, a lateral side surface 110*b*, a posterior side surface 112*a*, and an anterior side surface 112*b*. It is to be understood that since plate portion 104 is substantially oval, these side surfaces may not have distinct boundaries. Preferably, medial side surface 110*a* and top surface 108 define an edge 118*a*, and lateral side surface 110*b* and top surface 108 define an edge 118*b*. Preferably, posterior side surface 112*a* and top surface 108 define an edge 120*a* (as shown in FIGS. 3, 13, and 23), and anterior side surface 112*b* and top surface 108 define an edge 120*b* (as shown in FIG. 1).

Figure 26:
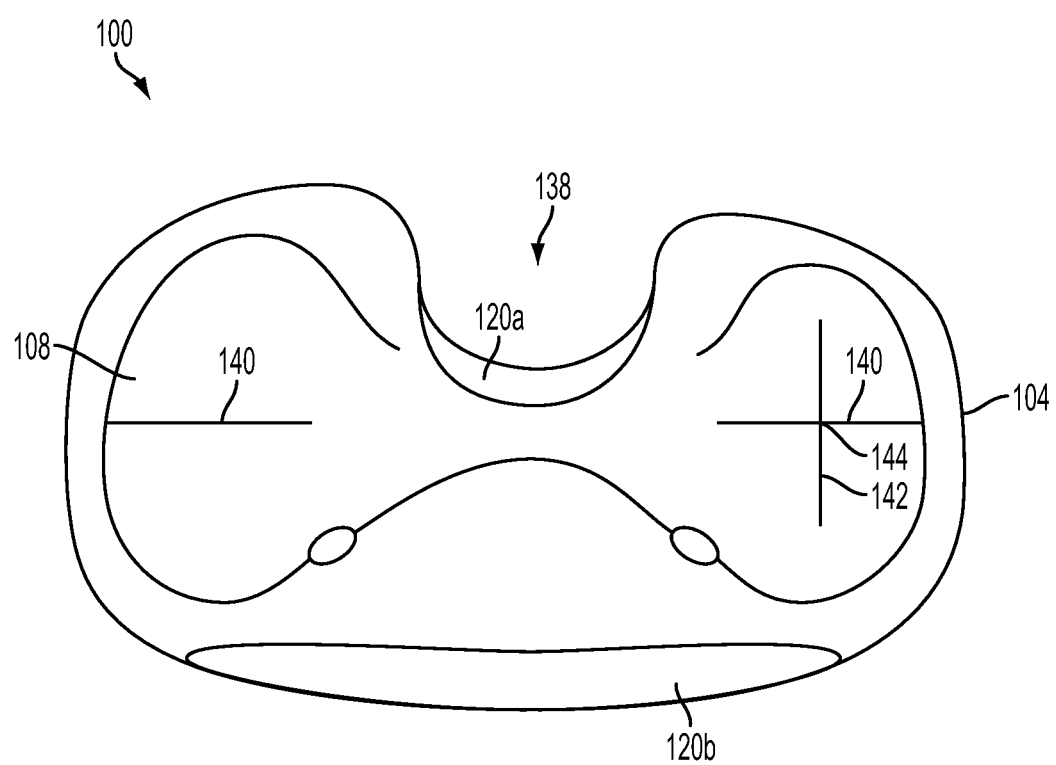
FIG. 26 is a top view of prosthetic of FIG. 1.
Figure 27:
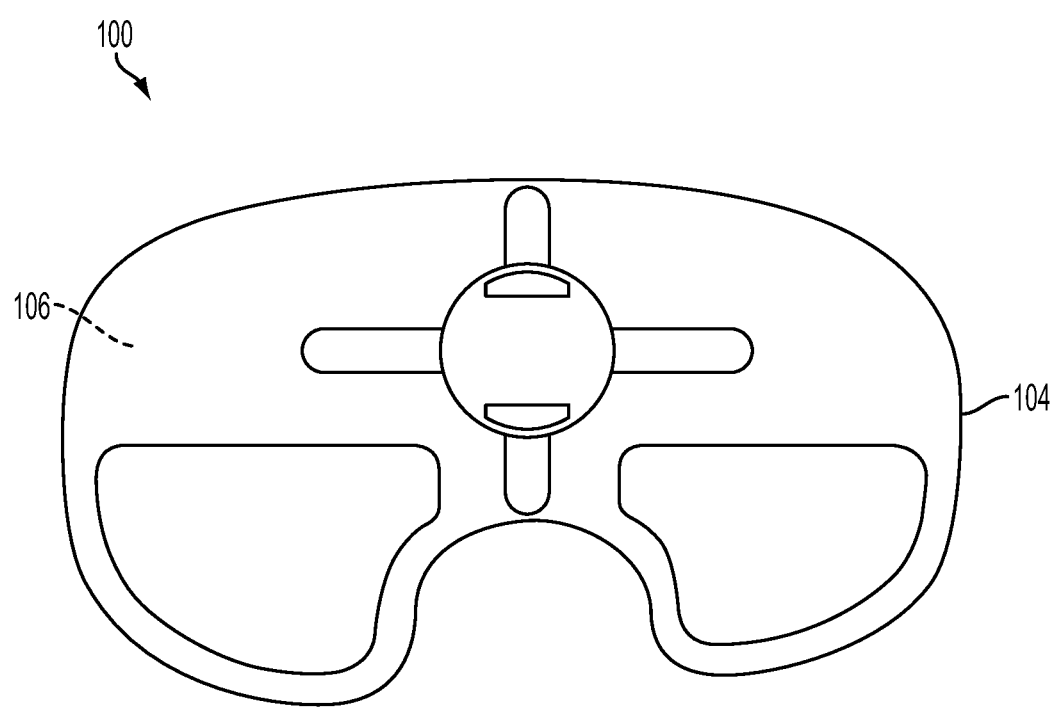
FIG. 27 is a bottom plan view of prosthetic of FIG. 1.

As used herein, edges 118*a* and 118*b* may be referred to herein singularly and collectively as "118" (FIG. 13, 23) and edges 120*a* and 120*b* may be referred to singularly and collectively as "120" (FIG. 26). It is to be understood that edges 118 and/or edges 120 may be a line, or substantially linear and/or edges 120 may be a line, or substantially linear and/or edges 120 may be a line or substantially linear and/or edges 118 and/or 120 may have a surface area (i.e., plan).

Figure 12:
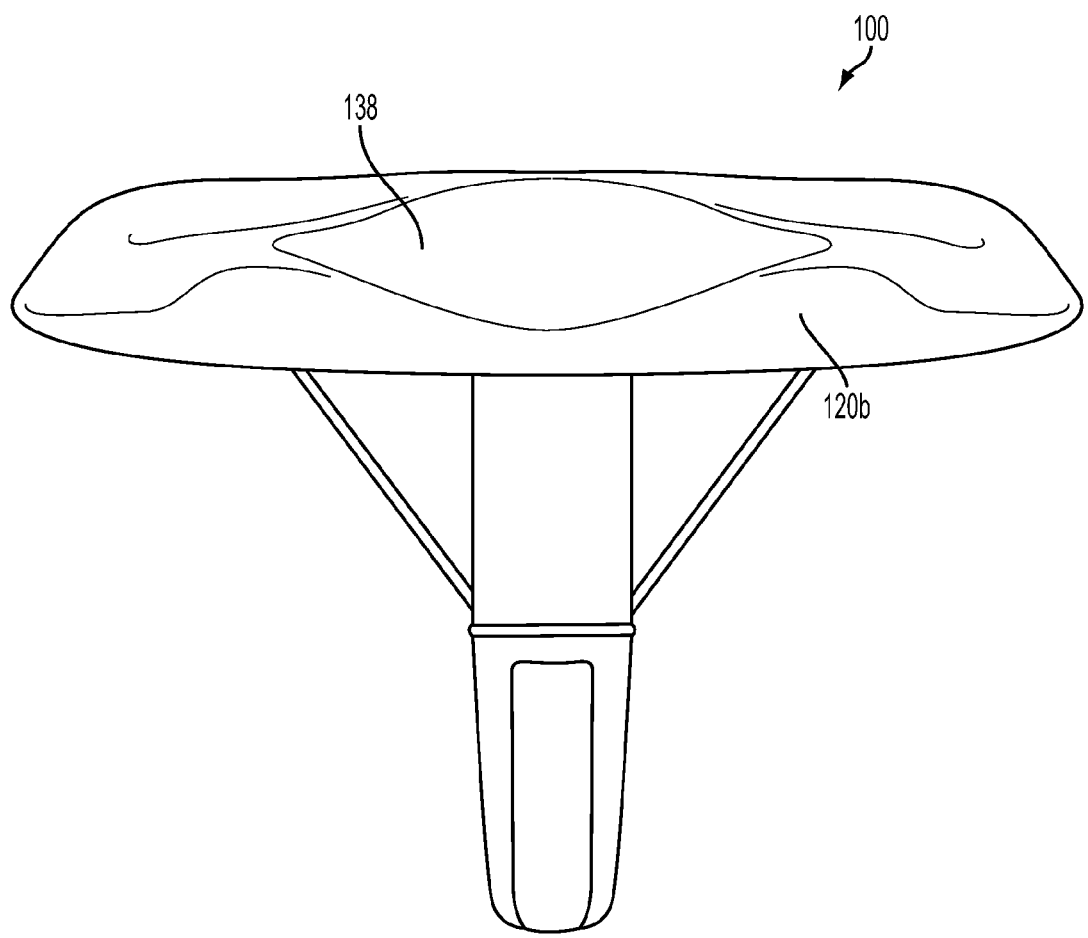
FIG. 12 is an anterior view of the prosthetic of FIG. 1.

In a preferred embodiment, and referring to FIGS. 1, 12, and 13, anterior side surface 112*b* comprises an indentation 138 and/or any other part of knee and/or component. Preferably, indentation 138 has an oblique edge. As such, anterior side edge 120*b* may refer to the preferably oblique edge at indentation 138. Preferably, indentation 138 prevents anterior knee pain and knee discomfort, for example, in extreme flexion. Preferably, indentation prevents, for example, the problem of patella jump while trying to do extension from extreme flexion. In other embodiments, indentation 138 is omitted. It is to be understood that indentation 138 may be of any shape/size, depending on, for example, the size of prosthetic 100. In addition, any other suitable structure may be used in lieu of, or in addition to, indentation 138. In other embodiments, indention 138 does not have an oblique edge.

Figure 21:
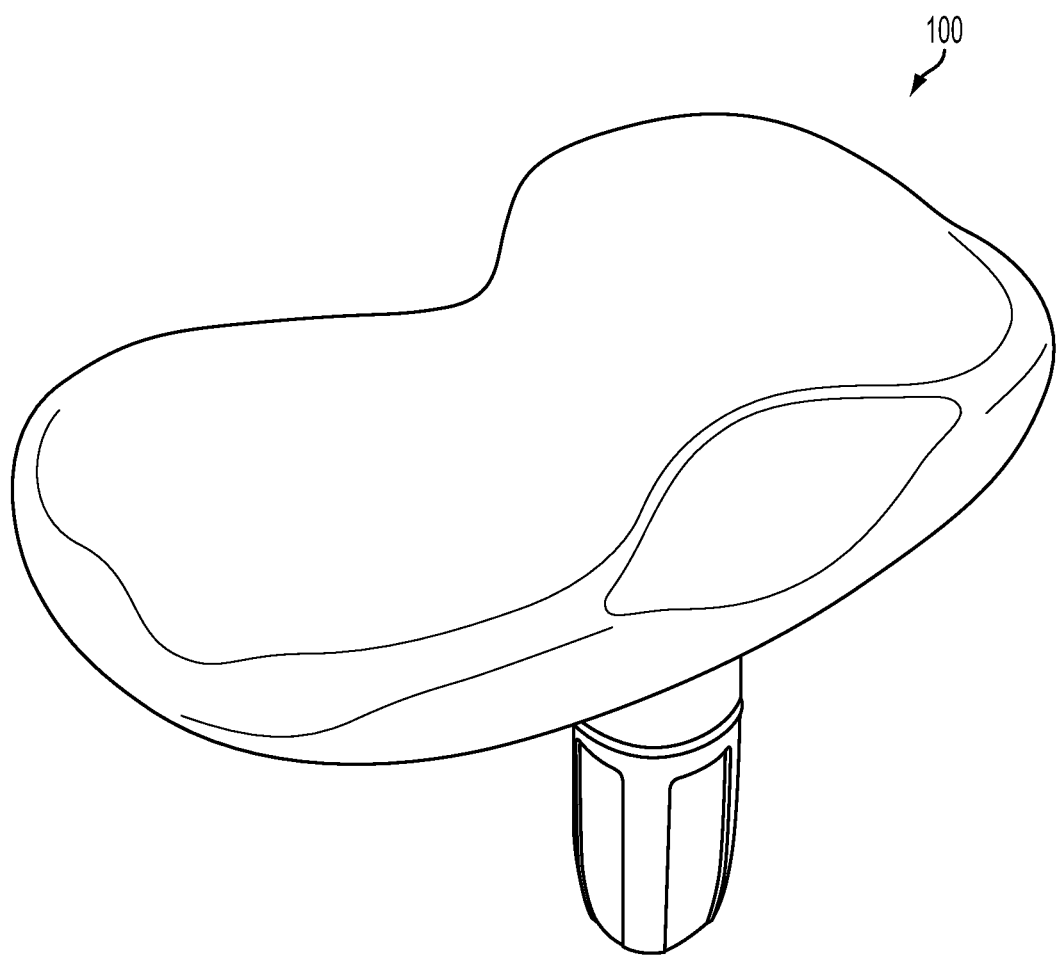
FIG. 21 is a perspective view of the prosthetic of FIG. 1
Figure 22:
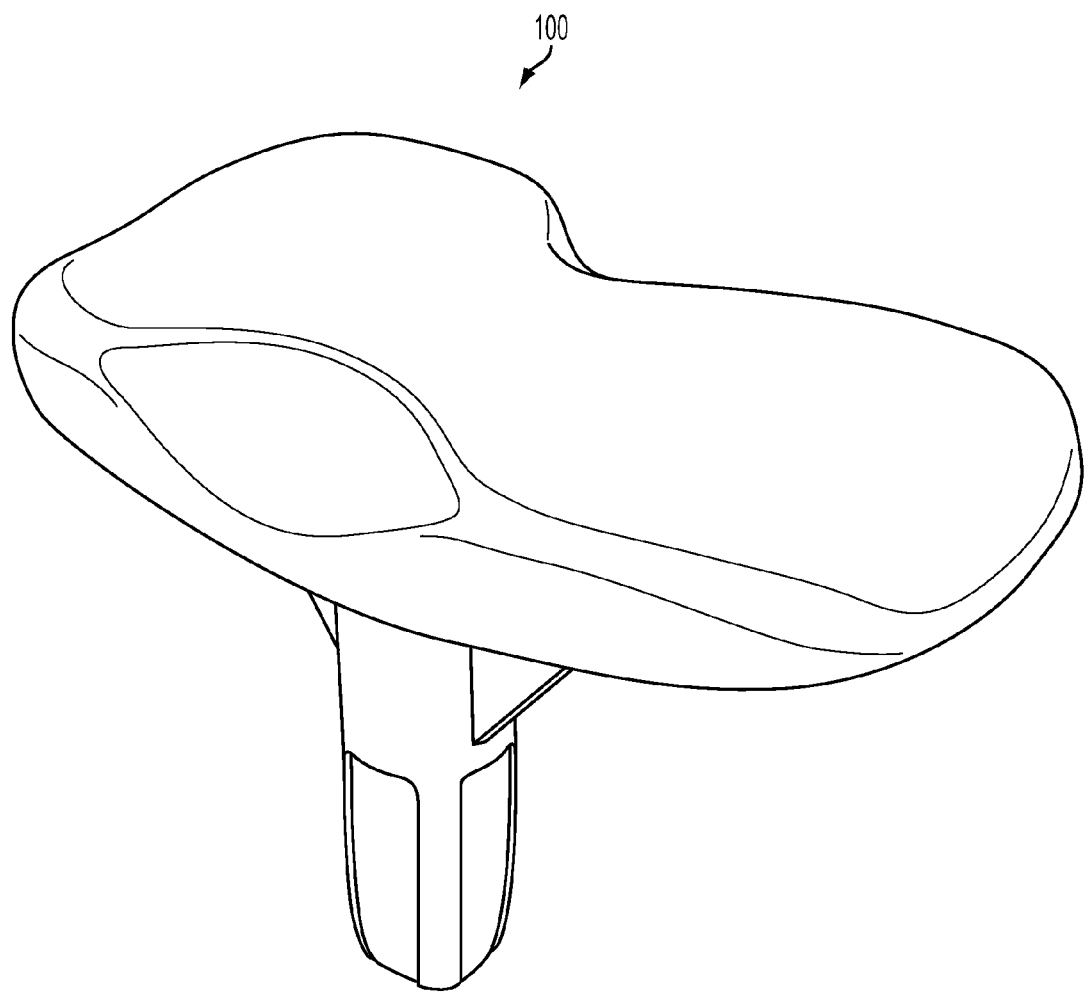
FIG. 22 is a perspective view of the prosthetic of FIG. 1.

In a preferred embodiment, and referring to FIG. 25, top surface 108 comprises a medial recess 116*a* for receiving a medial condyle 136*a* (not shown) of a femur and/or femoral component and a lateral recess 116*b* for receiving a lateral condyle 136*b* (not shown) of a femur and/or femoral component on its articulating surface. As used herein, recesses 116*a* and 116*b* may be referred to as "116" singularly and collectively. Preferably, recesses 116 are situated on either side of middle portion 146. Preferably, recesses 116 and middle portion 146 form an arch as shown in FIGS. 11 and 21, 25. In this regard, and as used herein, "arch" may refer to the middle portion 146 being not as defined (i.e., the boundary between each of the recesses 116 and middle portion 146 is not as defined). Preferably, each of medial recess 116*a* and lateral recess 116*b* is oval or substantially oval in shape.

In a preferred embodiment, and referring to FIG. 26, the long axis width 140 of recess 116 is from about 50 mm to about 80 mm, and the short axis length 142 of recess 116 is from about 30 mm to about 55 mm. Preferably, recess 116 is from about 6 mm to about 15 mm in depth at center 144. In other embodiments, the long axis width 140 may be less than about 50 mm or greater than about 80 mm; the short axis length 142 may be less than about 30 mm or greater than about 55 mm; and/or the depth at center 144 (as shown in FIG. 26) may be less than about 6 mm or greater than about 15 mm, without departing from the scope of the invention.

Preferably, between recesses 116 is middle portion 146. In other embodiments, each of medial recess 116a and lateral recess 116b may have any long axis width and/or short axis lengths, depending for example, on the size of the knee/size of the prosthetic implanted and/or they may have known widths/lengths (as shown in FIG. 26). For example, since prosthetic 100 preferably comprises an arch, and, in this regard, middle portion 146 may not be as defined, i.e., medial recess 116a and/or lateral recess 116b may be larger than what is currently known in the art. Additionally, it is to be understood that medial and lateral recesses 116 may or may not be symmetrical to each other. In yet other embodiments, medial recess and/or lateral recess is any other shape, i.e., not oval or substantially oval. In yet other embodiments, arch is omitted. In other embodiments, medial recess and/or lateral recess is omitted.

In a preferred embodiment, one or more of the edges are oblique or sloping (or are "oblique edges"). The oblique edge may be of a plane that is different from the plane of the side surface and the plane of the top surface 108. It is to be understood that one or more of these oblique edges may be curved and/or sloping. Preferably, and as discussed further below, these oblique edges allow for better natural knee movement, such as when sitting cross-legged and/or other instances that require extreme flexion. The sloping edge allows more room for, for example, the condyles to articulate about top surface 108 of plate portion 104. The inventive oblique/sloping edges of the subject invention will be described further below in terms of height and degree of incline/sloping.

Figure 4:
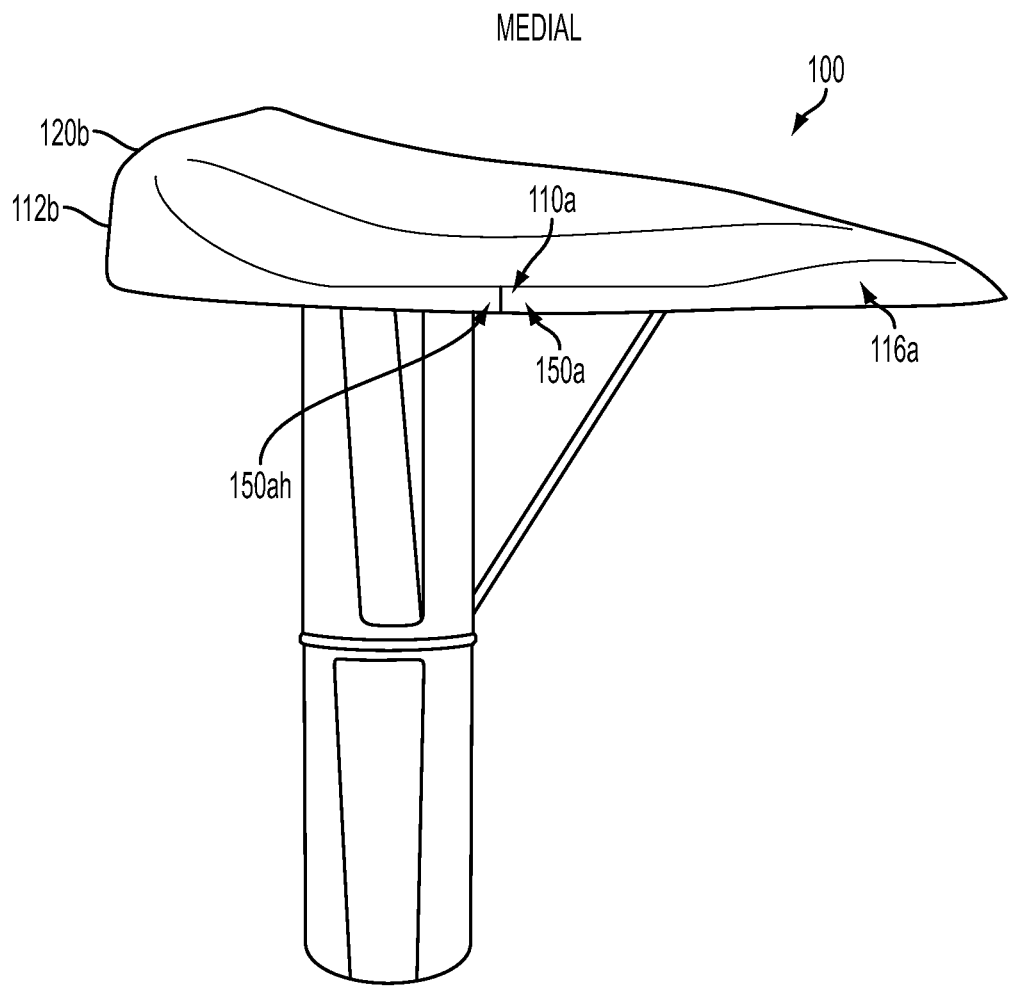
FIG. 4 is a side view of the prosthetic of FIG. 1.
Figure 5:
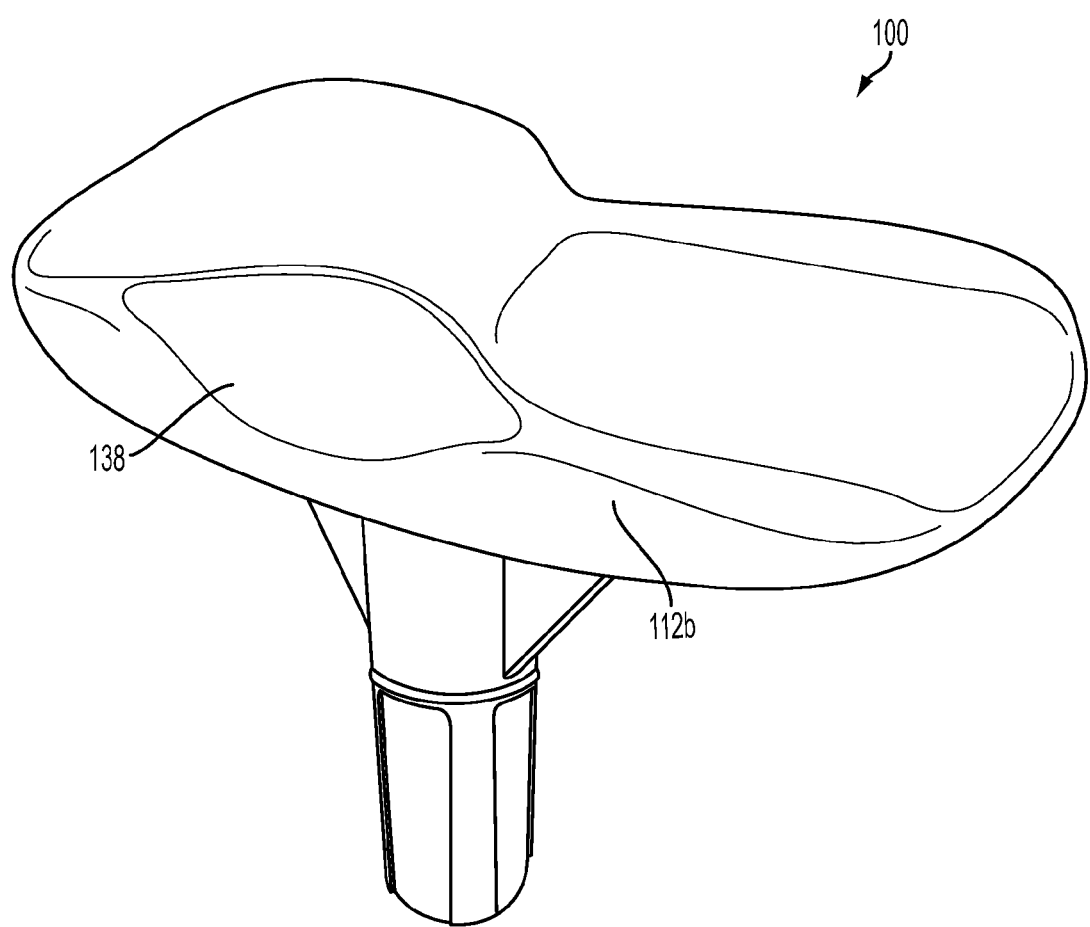
FIG. 5 is a perspective view of the prosthetic of FIG. 1.
Figure 6:
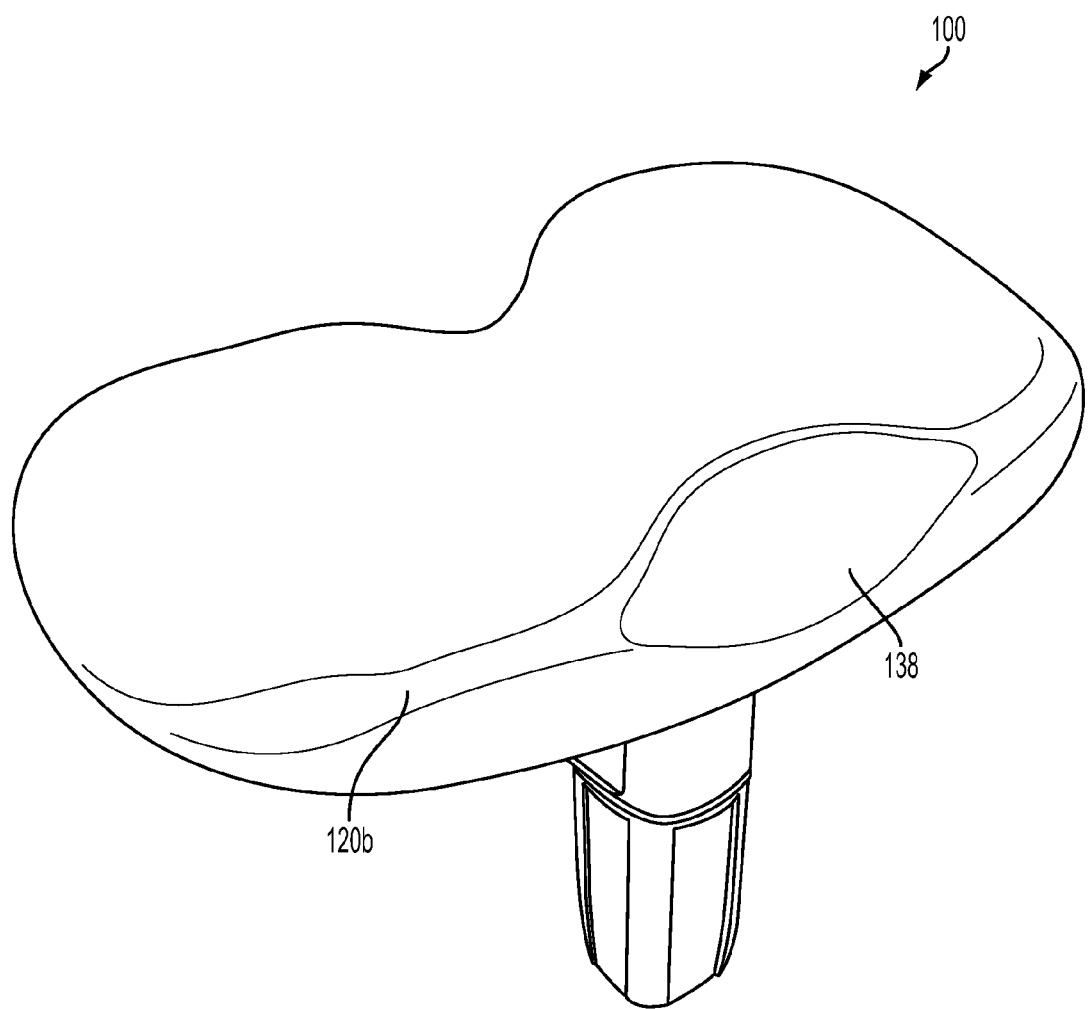
FIG. 6 is a perspective view of FIG. 1.
Figure 8:
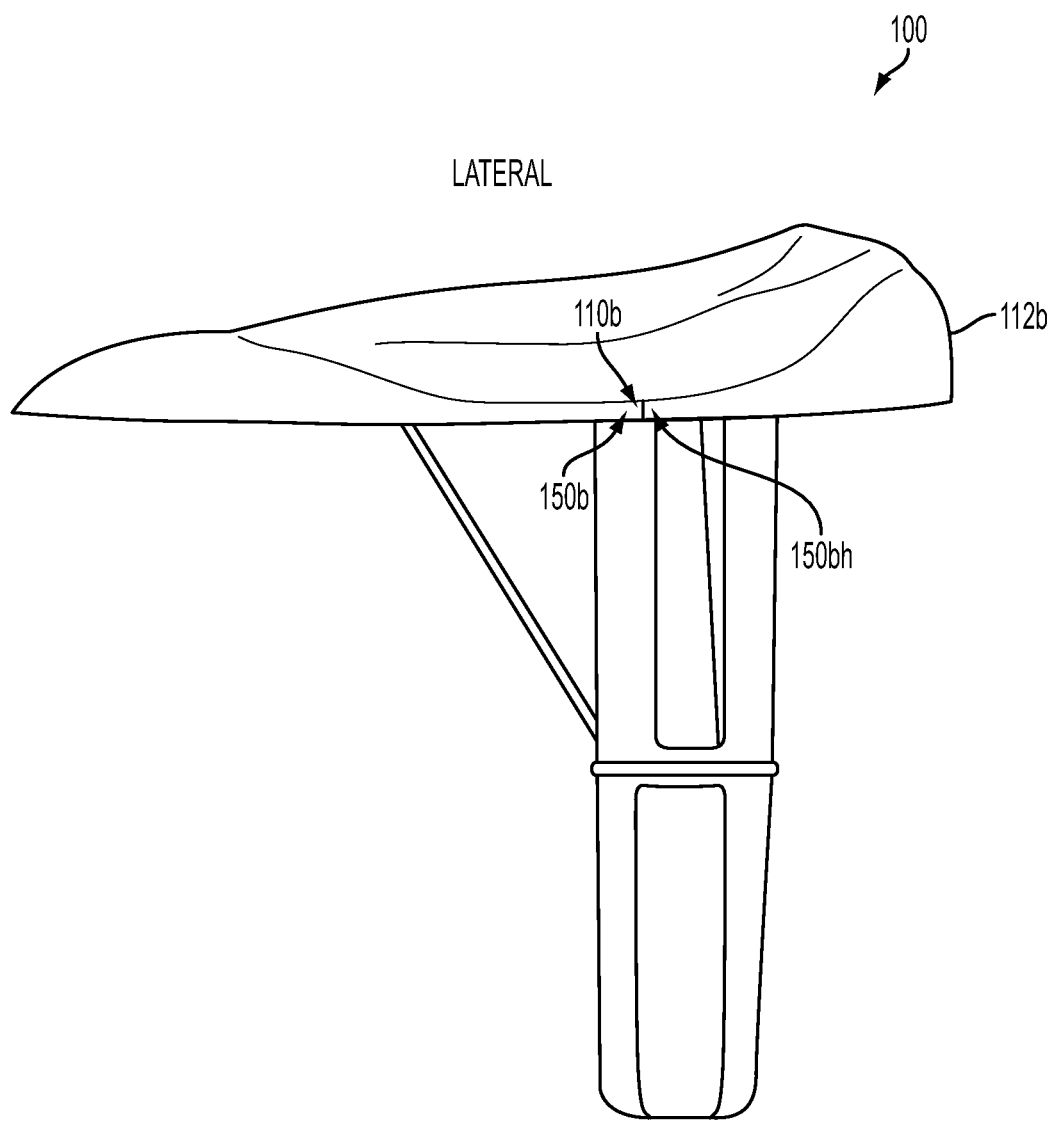
FIG. 8 is a side view of prosthetic of FIG. 1.
Figure 9:
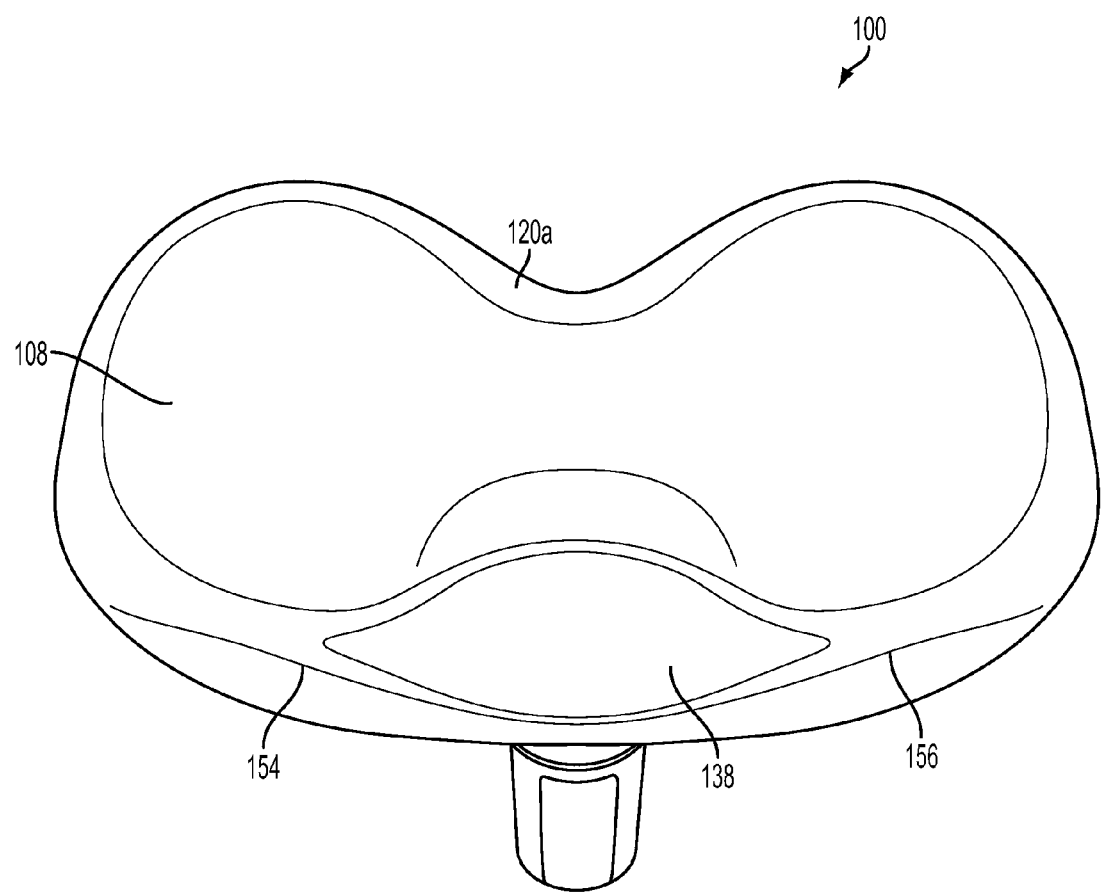
FIG. 9 is a top plan view of prosthetic of FIG. 1.
Figure 10:
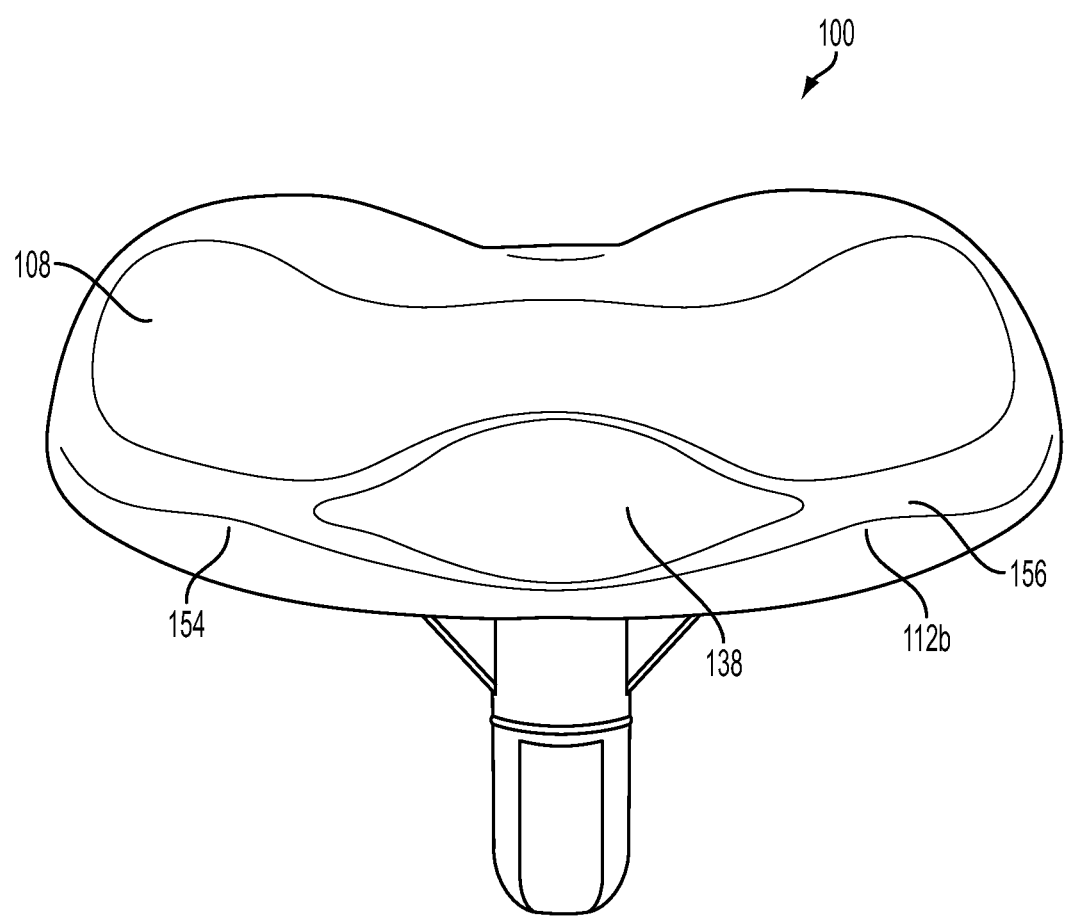
FIG. 10 is a top plan view of the prosthetic of FIG. 1.

In a preferred embodiment, medial side surface 110a comprises a medial side surface center axis 150a (as shown in FIG. 4); lateral side surface 110b comprises a lateral side surface center axis 150b (as shown in FIG. 8); anterior side surface 112b comprises an anterior side surface center axis 152b (as shown in FIG. 1 and FIG. 25); and posterior side surface 112a comprises a posterior side surface center axis 152a (as shown in FIG. 11). Preferably, anterior side surface center axis 152b is situated at indentation 138 (as shown in FIG. 1). In other embodiments, anterior side surface center axis 152b is not situated at indentation 138. For example, the size of medial portion 104a and/or lateral portion 104b may dictate whether anterior side surface center axis 152b is at indentation 138 or not. It is to be understood that each axis is at center of, or substantially at the center of, each side surface. In other embodiments, the one or more center axis described above is omitted.

In a preferred embodiment, at medial side surface center axis 150a, height 150ah (FIG. 4) is from about 6 mm to about 14 mm; more preferably from about 8 mm to about 12 mm; and most preferably from about 12 mm; and most preferably from about 9 mm to about 10 mm. In other embodiments, height 150ah may be more than about 14 mm or less than about 6 mm. It is to be understood that edge 118a may be sloping. As such, and for sake of simplicity, height 150ah is measured from bottom surface 106.

In a preferred embodiment, at lateral side surface center axis 150b, height 150bh (FIG. 8) is from about 7 mm to about 14 mm; more preferably from about 8 mm to about 12 mm; and most preferably from about 9 mm to about 10 mm. In other embodiments, height 150bh is less than about 7 mm or greater than about 14 mm. It is to be understood that edge 118b may be sloping. As such, and for the sake of simplicity, height 150ah is measured from bottom surface 106.

In a preferred embodiment, at posterior side surface center axis 152a, height 152ah is from about 6 mm to about 12 mm; more preferably from about 7 mm to about 11 mm; and most preferably from about 8 mm to about 10 mm. In other embodiments, height 152ah is less than about 6 mm or greater than about 12 mm. It is to be understood that edge 120 may be sloping. As such, and for the sake of simplicity, height 152ah is measured from bottom surface 106.

In a preferred embodiment, an anterior side center axis 152b, height 152bh (as shown in FIG. 1 and FIGS. 25A-D) is from about 7 mm to about 20 mm; more preferably from about 8 mm to about 18 mm; most preferably from about 9 mm to about 16.5 mm. In other embodiments, height 152bh is less than about 7 mm or greater than about 20 mm. It is to be understood that the edge 120b (FIG. 26) may be sloping. As such, and for sake of simplicity, height 152bh is measured from bottom surface 106. It is to be understood that height 152bh is preferably measured at indention 138. Additionally, it is to be understood that anterior side surface center axis height 152bh is preferably greater than posterior side surface center axis height 152bh. In other embodiments, however, height 152ah is not measured from indentation 138.

In a preferred embodiment, and as shown in FIG. 1, anterior side surface 112b includes a first protrusion 154 and a second protrusion 156. Protrusion 154 comprises a protrusion center axis 154a and protrusion 156 comprises a protrusion center axis 156a. preferably, protrusion center axis 154a comprises a height 154ah at center axis 154a and protrusion center axis 156a comprises a height 156ah at center axis 156a.

In a preferred embodiment, height 154ah and/or height 156ah may be from about 10 mm to about 15 mm; more preferably from about 12 mm to about 14 mm; and most preferably from about 12.5 mm to about 13.5 mm. In other embodiments, height 154ah and/or height 156ah may be greater than about 15 mm or less than about 10 mm.

In a preferred embodiment, height 152ah is about 2.5 mm greater than each of height 154ah and 156ah. Currently, prosthetics have a posterior side surface height at indentation 138 (or any other opening for receiving a PCL) relative to the height of the protrusions on either side of the opening for receiving a PCL. In a preferred embodiment of present invention, however, this ratio/relationship between the height at the opening and/or indentation and the height at each of the protrusions is increased. Preferably, the greater difference in height in the present invention preferably prevents anterior subluxation or dislocation. In other embodiments, height 152ah is not greater than (or about 2.5 greater than) each of heights 154ah and/or 156ah and/or may be the same or similar to what is currently known in the art. In some embodiments, height 152bh is 2.5 times greater than height 152ah.

In a preferred embodiment, edge 118a is oblique. Preferably, edge 118a is oblique from about 0 to about 75 degrees; more preferably, from about 15 degrees to about 60 degrees; most preferably, from about 30 to about 45 degrees. In other embodiments, edge 118a is not oblique. In yet other embodiments, edge 118a is oblique less than about 10 degrees or greater than about 75 degrees. In yet other embodiments, edge 118a is not oblique (as shown in FIG. 23).

In a preferred embodiment, edge 118b is oblique. Preferably, edge 118b is oblique from about 10 degrees to about 75 degrees; more preferably, from about 15 degrees to about 60 degrees; and most preferably, from about 30 to about 45 degrees. In other embodiments, edge 118b is not oblique. In yet other embodiments, edge 118b is oblique less than about 10 degrees or greater than about 75 degrees. In yet other embodiments, edge 118b is not oblique (as shown in FIG. 23).

In a preferred embodiment, edge 120a is oblique (as shown in FIGS. 9 and 11). Preferably, edge 120a is oblique from about 10 degrees to about 75 degrees; more preferably, from about 15 to about 60 degrees; and most preferably, from about 30 to about 45 degrees. In other embodiments, edge 120a is not oblique. In yet other embodiments, edge 120a is oblique less than about 10 degrees or greater than about 75 degrees.

In a preferred embodiment, and referring to FIG. 12, edge 120b is oblique. Preferably, edge 120b is oblique from about 10 degrees to about 75 degrees; more preferably, from about 15 to about 60 degrees; and most preferably, from about 30 to about 45 degrees. Preferably, edge 120b is oblique at indentation 138. In other embodiments, edge 120b is not oblique. In yet other embodiments, edge 120b is not oblique. In yet other embodiments, edge 120b is oblique less than about 10 degrees or greater than about 75 degrees.

In a preferred embodiment, each of edge 118a, 118b, 120a, 120b, and indentation 138 is oblique and/or sloping (as shown in FIGS. 1, 11, 12, and 23). In other embodiments, one or more of the foregoing edges, but not all, may be oblique. The height at each side surface and/or degree of incline/sloping may be based on a variety of factors, for example, on size of prosthetic 100 and/or whether femoral component 130 is used or not, etc.

In a preferred embodiment, tibial portion 102 and plate portion 104 are made of durable, wear-resistant, shock-absorbing, biocompatible material. Preferably, tibial portion 102 and plate portion 104 are comprised of polyethylene, or the like. Preferably, tibial portion 102 and plate portion 104 consists of any biocompatible material. Preferably, tibial portion 102 and portion 104 do not comprise a metal and/or consist essentially of a metal and/or comprise a metal. Preferably prosthetic 100 is manufactured in a milling, casting, injection molding, sanding, polishing and/or any other suitable manufacturing and finishing process. In other embodiments, prosthetic 100 comprises a metal.

In a preferred embodiment, a metal plate (or metal-backed plate, as is known in the art) is not disposed between tibial portion 102 and plate portion 104. As such, there is no need for a locking mechanism between a metal plate and plate portion 104 in the present invention. As such, there is less or no backside wear and/or micromovements between two surfaces. In other embodiments, and as shown in FIG. 28, prosthetic 100 does not include tibial portion 102. In these embodiments, prosthetic 100 includes plate portion 104 as described herein, a metal plate portion 180, and/or an appropriate locking mechanism 182. Locking mechanism 182 as referred to herein may consist of bottom portion of plate portion 104 and a top portion of metal plate portion 180. A top portion of metal plate portion 180 may comprise a corresponding slot to fit into locking mechanism 182. Metal plates/portions, or metal-backed plates/portions, are known in the art and may be available from, for example, Zimmer.

In a preferred embodiment, prosthetic 100 allows for a greater range of natural knee movement. For example, the one or more beveled/sloping edges on plate 104 provide more space for any femur/femoral component articulating on plate 104 to move/rotate over plate 104. As such, the knee has a greater range of motion. For example, its design and/or composition allow for better flexion of the knee. Preferably, patients having prosthetic 100 allows for rotation of femur/femoral component over it (as such, patients may be able to sit on the floor cross-legged). Preferably, use of prosthetic 100 allows for flexion up to about 150 degrees.

In a preferred embodiment, prosthetic 100 has many advantages. For example, use of prosthetic 100 of the present invention, allows for little or no metal to be placed inside the human body; thereby, there is less chance for infection. Furthermore, use of prosthetic 100 preserves more bone. Additionally, it is cost-effective. Its use reduces and/or eliminates the problems associated with a prosthetic having a locking mechanism.

In a preferred embodiment, prosthetic 100 is implanted with known methods. For example, the worn tibia is resected and/or prepared (i.e., the damaged part of the joint is removed from the surface of the bones), and the surfaces are shaped to hold prosthetic 100 and/or any other joint component, i.e., a femoral component 130. Prosthetic 100 is attached to the tibia/knee cap with either cement or special material or without it. When fit together, prosthetic 100 (and any other joint parts implanted) form the joint, relying on the surroundings muscles and ligaments for support and function. Currently, prosthetics comprise metal-backed meniscal components that have rotating platforms. Preferably, however, the present invention does not comprise a rotating component.

The foregoing embodiments are merely examples of the present invention. Those skilled in the art may make numerous uses of and departures from, such embodiments, without departing from the scope and spirit of the present invention. Accordingly, the scope of the present invention is not to be limited or defined by such embodiments in any way, but rather, is defined solely by the following claims.

What is claimed is:

1. A knee replacement system comprising a prosthetic having:
   a tibial portion implantable on a resected surface of a tibia;
   a plate portion attached to the tibial portion and at least partially implantable in a meniscal space, wherein the plate portion comprises:
      a top surface having a medial recess and a lateral recess for receiving a medial condyle and a lateral condyle of a femur or a femur component, wherein an inner middle lateral side of the medial recess forms a first portion of an arched shaped middle portion of the top surface and an inner middle medial side of the lateral recess forms a second portion of the arched shaped middle portion of the top surface;
      a bottom surface attached to a top surface of the tibial portion;
      a medial side surface attached to a medial side of the top surface and a medial side of the bottom surface and defining a medial side edge, wherein the medial side edge is oblique with respect to at least a portion of the medial side of the top surface;
      a lateral side surface attached to a lateral side of the top surface and a lateral side of the bottom surface and defining a lateral side edge, wherein the lateral side edge is oblique with respect to at least a portion of the lateral side of the top surface;
      a posterior side surface attached to a posterior side of the top surface and a posterior side of the bottom surface and defining a posterior side edge, wherein the posterior side edge is oblique with respect to at least a portion of the posterior side of the top surface; and
   wherein a combination of the oblique lateral side edge, the oblique medial side edge and the arched shaped middle portion is configured so as to allow for a cross legged sitting position, wherein the femur or the femur component may rotate in the posterior and lateral direction such that an anterior part of the medial condyle of the femur or the femur component is able to slide over the arched shaped middle portion while a posterior part of the medial condyle of the femur or the femur component is able to slide over the oblique medial side edge of the plate portion and while simultaneously an anterior part of the lateral condyle is able to slide over the oblique lateral side edge and a posterior part of the lateral condyle of the femur or the femur component is able to slide over the oblique posterior side edge to allow for the cross legged sitting position.

2. The knee replacement system of claim 1, wherein the tibial portion includes:
   a tibial stem, wherein at least a portion of the tibial stem is implanatable on the tibia; and
   wherein the prosthetic including the plate portion and the tibial portion consists essentially of a polyethylene.

3. The knee replacement system of claim 1, wherein the plate portion further comprises:
   an anterior side surface attached to an anterior side of the top surface and an anterior side of the bottom surface and defining an anterior side edge, wherein the anterior side edge is oblique with respect to at least a portion of the anterior side of the top surface.

4. The knee replacement system of claim 3, wherein the posterior side edge is oblique from 15 to 60 degrees with respect to the portion of the posterior side of the top surface.

5. The knee replacement system of claim 3, wherein the anterior side edge is oblique from 15 to 60 degrees with respect to the portion of the anterior side of the top surface.

6. The knee replacement system of claim 1, wherein the medial side edge is oblique from 15 to 60 degrees with respect to the portion of the medial side of the top surface and the lateral side edge is oblique from 15 to 60 degrees to the portion of the lateral side of the top surface.

7. The knee replacement system of claim 1, further comprising the femur component, wherein the femur component comprises the medial condyle and the lateral condyle, wherein the femur component is at least partially implantable on a resected portion of the femur.

8. The knee replacement system of claim 1, wherein the arched shaped middle portion of the top surface further comprises:
   an upwardly curved arch between the first portion and the second portion of the arched shaped middle portion of the top surface.

9. The knee replacement system of claim 1, wherein the tibial portion is a metal-backed tibial portion attached to the plate portion.

10. The knee replacement system of claim 1, wherein the first and second portions of the arched shaped middle portion are smoothly continuous to provide for the femur or the femur component to slide on the plate portion allowing for the cross legged sitting positioning.

11. A knee replacement system comprising a prosthetic, wherein the prosthetic comprises:
   a tibial portion;
   a plate portion attached to the tibial portion and at least partially implantable in a meniscal space, wherein the plate portion comprises:
      a top surface having a medial recess and a lateral recess for receiving a medial condyle and a lateral condyle of a femur or a femur component, wherein an inner middle lateral side of the medial recess forms a first portion of an arched shaped middle portion of the top surface and an inner middle medial side of the lateral recess forms a second portion of the arched shaped middle portion of the top surface;
      a medial side surface attached to a medial portion of the top surface and a medial portion of a bottom surface and defining a medial side edge, wherein at least a portion of the medial side edge is oblique with respect to the medial portion of the top surface;
      a lateral side surface attached to a lateral portion of the top surface and a lateral portion of the bottom surface and defining a lateral side edge, wherein at least a portion of the lateral side edge is oblique with respect to the lateral portion of the top surface;
      a posterior side surface attached to a posterior portion of the top surface and a posterior portion of the bottom surface and defining a posterior side edge, wherein at least a portion of the posterior side edge is oblique with respect to the posterior portion of the top surface; and
      an anterior side surface attached to an anterior portion of the top surface and an anterior portion of the bottom surface and defining an anterior side edge, wherein at least a portion of the anterior side edge is oblique with respect to the anterior portion of the top surface;
      wherein the top surface is configured such that during movement to a cross legged sitting position, the femur or the femur component is able to rotate in a posterior and lateral direction such that an anterior portion of the medial condyle of the femur or femur component is able to slide over the arched shaped middle portion while a posterior portion of the medial condyle of the femur or femur component is able to simultaneously slide over the oblique medial side edge of the plate portion; and
      wherein during the movement to the cross legged sitting position and simultaneous with the movement of the medial condyle, an anterior portion of the lateral condyle of the femur or femur component is able to slide over the oblique lateral side edge and a posterior portion of the lateral condyle of the femur or femur component is able to slide over the oblique posterior side edge to allow for the cross legged sitting position.

12. The knee replacement system of claim 11, wherein the tibial portion includes:
   a tibial stem, wherein at least a portion of the tibial stem is implanatable on a tibia; and
   wherein the prosthetic including the plate portion and the tibial portion is comprised essentially of plastic.

13. The knee replacement system of claim 11, wherein the anterior side surface comprises:
   a first protrusion; and
   a second protrusion, wherein the first protrusion and the second protrusion form an indentation therebetween.

14. The knee replacement system of claim 13, wherein the indentation forms an oblique edge with respect to the anterior portion of the top surface.

15. The knee replacement system of claim 13, wherein the first protrusion includes a first protrusion center axis, the second protrusion includes a second protrusion center axis, and the posterior side surface includes a posterior side surface center axis; and
   wherein a height of the first protrusion at the first protrusion center axis from the top surface to the bottom surface is greater than a height of the posterior side surface at the posterior side surface center axis from the top surface to the bottom surface and a height of the second protrusion at the second protrusion center axis from the top surface to the bottom surface is greater than the height of the posterior side surface at the posterior side surface center axis.

16. The knee replacement system of claim 11, wherein a height at an anterior side surface center axis from the top surface to the bottom surface is greater than a height at a posterior side surface center axis from the top surface to the bottom surface.

17. The knee replacement system of claim 16, wherein the height at the anterior side surface center axis from the top surface to the bottom surface is at least 2.5 times greater than the height at the posterior side surface center axis from the top surface to the bottom surface.

18. A knee replacement system comprising a prosthetic, wherein the prosthetic comprises:
a plate portion at least partially implantable in a meniscal space, wherein the plate portion comprises:
a top surface having a medial recess and a lateral recess for receiving a medial condyle and a lateral condyle of a femur or a femur component, wherein an inner middle lateral side of the medial recess forms a first portion of an arched shaped middle portion of the top surface and an inner middle medial side of the lateral recess forms a second portion of the arched shaped middle portion of the top surface;
a medial side surface adjacent a medial portion of the top surface and a medial portion of a bottom surface and defining a medial side edge, wherein a portion of the medial side edge is oblique with respect to the medial portion of the top surface;
a lateral side surface adjacent to a lateral portion of the top surface and a lateral portion of the bottom surface and defining a lateral side edge, wherein a portion of the lateral side edge is oblique with respect to the lateral portion of the top surface;
a posterior side surface adjacent to a posterior portion of the top surface and a posterior portion of the bottom surface and defining a posterior side edge;
an anterior side surface adjacent to an anterior portion of the top surface and an anterior portion of the bottom surface and defining an anterior side edge; and
wherein a height at an anterior side surface center axis from the top surface to the bottom surface is greater than a height at a posterior side surface center axis from the top surface to the bottom surface;
wherein a structure of the combination of the arched shaped middle portion and the oblique portion of each of the medial side edge, the lateral side edge and the posterior side edge provide for rotation of a femur or a femur component in both a posterior and lateral direction on the plate portion during movement to a cross legged sitting position that requires extreme flexion, wherein the top surface is configured such that an anterior part of a medial condyle of the femur or femur component is able to slide over the arched shaped middle portion while a posterior part of the medial condyle of the femur or femur component is able to slide over the oblique medial side edge of the plate portion and while simultaneously a posterior part of a lateral condyle of the femur or femur component is able to slide over the oblique posterior side edge and an anterior part of the lateral condyle is able to slide over the oblique lateral side edge to allow for the cross legged sitting position.

19. The knee replacement system of claim 18, wherein the height at the anterior side surface center axis from the top surface to the bottom surface is at least 2.5 times greater than the height at the posterior side surface center axis from the top surface to the bottom surface.

20. The knee replacement system of claim 18,
wherein at least a portion of the posterior side edge is oblique with respect to the posterior portion of the top surface; and
wherein at least a portion of the anterior side edge is oblique with respect to the anterior portion of the top surface.

* * * * *